(12) United States Patent
Shifrin et al.

(10) Patent No.: US 11,446,237 B2
(45) Date of Patent: Sep. 20, 2022

(54) STABLE TOPICAL COMPOSITIONS OF FENOLDOPAM

(71) Applicant: TARO PHARMACEUTICAL INDUSTRIES LTD., Haifa Bay (IL)

(72) Inventors: Helena Shifrin, Rehovot (IL); Alexandra Shraifel, Nahariya (IL); Vered Rosenberger, Givatayim (IL); Ron Schlinger, Tel Aviv (IL); Tzviel Sheskin, Haifa (IL); Avi Avramoff, Haifa (IL)

(*) Notice: Subject to any disclaimer, the term of this patent is extended or adjusted under 35 U.S.C. 154(b) by 0 days.

(21) Appl. No.: 17/430,264

(22) PCT Filed: Mar. 6, 2020

(86) PCT No.: PCT/IB2020/051967
§ 371 (c)(1),
(2) Date: Aug. 11, 2021

(87) PCT Pub. No.: WO2020/183322
PCT Pub. Date: Sep. 17, 2020

(65) Prior Publication Data
US 2022/0040089 A1   Feb. 10, 2022

Related U.S. Application Data

(60) Provisional application No. 62/815,893, filed on Mar. 8, 2019.

(51) Int. Cl.
| | | |
|---|---|---|
| A61K 9/14 | (2006.01) | |
| A61K 31/55 | (2006.01) | |
| A61K 47/32 | (2006.01) | |
| A61K 47/38 | (2006.01) | |
| A61P 17/06 | (2006.01) | |
| A61P 17/04 | (2006.01) | |
| A61K 9/00 | (2006.01) | |

(52) U.S. Cl.
CPC ............ *A61K 9/0014* (2013.01); *A61K 31/55* (2013.01); *A61K 47/32* (2013.01); *A61K 47/38* (2013.01); *A61P 17/04* (2018.01); *A61P 17/06* (2018.01)

(58) Field of Classification Search
CPC combination set(s) only.
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson | |
| 6,054,429 A | 4/2000 | Bowersox et al. | |
| 6,238,693 B1 | 5/2001 | Luther et al. | |
| 6,960,353 B2 | 11/2005 | van Osdol et al. | |
| 7,358,236 B1 | 4/2008 | Chaplin | |
| 7,592,332 B2 | 9/2009 | Cogan et al. | |
| 7,820,145 B2 | 10/2010 | Tamarkin et al. | |
| 8,859,001 B2 | 10/2014 | Levite et al. | |
| 9,161,916 B2 | 10/2015 | Tamarkin et al. | |
| 2004/0057987 A1 | 3/2004 | van Osdol | |
| 2008/0311657 A1 | 12/2008 | Levite | |
| 2009/0162371 A1 | 6/2009 | Benson et al. | |
| 2011/0104287 A1* | 5/2011 | Levite .................. | A61K 9/0024 424/489 |
| 2020/0345671 A1* | 11/2020 | Dhuppad ................. | A61K 9/06 |

FOREIGN PATENT DOCUMENTS

| | | | |
|---|---|---|---|
| JP | H1 1-335236 A | 12/1999 | |
| JP | 2011-144143 A | 7/2011 | |
| JP | 2016-034941 A | 3/2016 | |
| WO | 1996/000060 A1 | 1/1996 | |
| WO | 1999/55341 A1 | 11/1999 | |
| WO | 2000/004886 A1 | 2/2000 | |
| WO | 2005/079851 A2 | 9/2005 | |
| WO | 2009/052491 A2 | 4/2009 | |
| WO | 2009/076553 A1 | 6/2009 | |
| WO | 2010/014946 A2 | 2/2010 | |
| WO | 2012/052479 A2 | 4/2012 | |
| WO | 2012/148799 A1 | 11/2012 | |
| WO | 2013/178760 A1 | 12/2013 | |
| WO | WO-2016116909 A2 * | 7/2016 | ............. A61P 19/02 |
| WO | 2018/042352 A1 | 3/2018 | |

OTHER PUBLICATIONS

IN201741025273A Abstract Published Jan. 2019.*
Bonacucina et al., "Characterization and Stability of Emulsion Gels Based on Acrylamide/SodiumAcryoldimethylTaurate Copolymer," AAPS PharmSciTech, vol. 10, No. 2, Jun. 2009.*
Doppalapudi et al., "Fenoldopam mesylate for treating psoriasis: A new indication for an old drug," International Journal of Pharmaceuticals 573:118726 (2020).
FDA Clinical Pharmacology & Biopharmaceutics Review, NDA 19922 Corlopam dated Sep. 25, 1997.
The International Search Report and Written Opinion, WIPO Application No. PCT/IB2017/055224, dated Dec. 19, 2017.

(Continued)

*Primary Examiner* — Jared Barsky
(74) *Attorney, Agent, or Firm* — Medler Ferro Woodhouse & Mills PLLC

(57) ABSTRACT

The present disclosure is directed to a topical composition, e.g., a physically and chemically stable topical composition of Fenoldopam comprising about 0.1% to about 5% by weight of Fenoldopam or a pharmaceutically acceptable salt thereof, at least one polyacrylamide-type gelling agent, at least one cellulose-type gelling agent, and at least one solvent, wherein the Fenoldopam is substantially solubilized in the composition, and wherein the composition is stable for at least twelve months at 25° C. and 60% relative humidity.

20 Claims, 1 Drawing Sheet

(56) References Cited

OTHER PUBLICATIONS

The International Search Report and Written Opinion, WIPO Application No. PCT/IB2020/051967, dated May 18, 2020.
English translation of Japanese Office Action issued in JP Appl. No. 2019-532218, dated Jun. 8, 2021.
Keren et al., "Instantaneous depolarization of T cells via dopamine receptors, and inhibition of activated T cells of Psoriasis patients and inflamed human skin, by D1-like receptor agonist: fenoldopam" *Immunology* 158(3)171-193 (2019).

\* cited by examiner

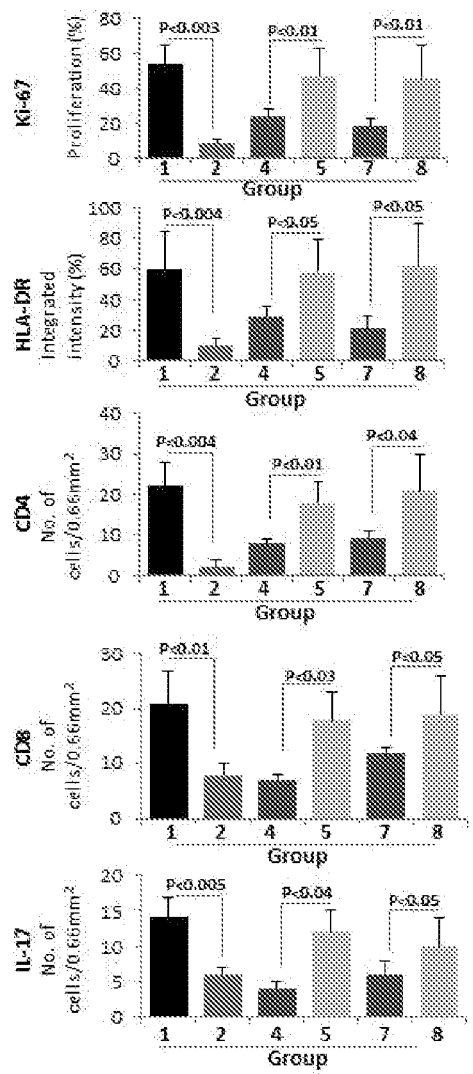

STABLE TOPICAL COMPOSITIONS OF FENOLDOPAM

FIELD OF THE INVENTION

The present disclosure is directed to a topical Fenoldopam composition, e.g., a physically and chemically stable topical composition of Fenoldopam comprising about 0.1% to about 5% by weight of Fenoldopam or a pharmaceutically acceptable salt thereof, at least one polyacrylamide-type gelling agent, at least one cellulose-type gelling agent, and at least one solvent, wherein the Fenoldopam is substantially solubilized in the composition, and wherein the composition is stable for at least 12 months at 25° C. and 60% relative humidity.

BACKGROUND

Psoriasis is a skin disease affecting many people worldwide. Beyond its dermatological manifestations, psoriasis may have significant impact on a patient's quality of life. Psoriasis is a chronic, immune-mediated, inflammatory skin disorder characterized by epidermal hyperproliferation of keratinocytes and endothelial cells, and the accumulation of inflammatory cells (e.g., activated T cells). Chronic plaque psoriasis, referred to as psoriasis vulgaris, is a common form of the disease and is characterized by well-demarcated, erythematous, scaly plaques, which may involve any part of the skin but commonly the extensor surfaces (such as the elbows and knees) and the scalp.

Treatments for psoriasis include topical agents, photo-based therapies, traditional systemic drugs and biologic agents. Treatment approach is often driven by disease severity. Patients presenting mild psoriasis may be treated with topical anti-inflammatory corticosteroids. However, it has been reported that long-term use of corticosteroids may lead to either systemic or local severe side-effects. Patients with moderate to severe forms of psoriasis may undergo systemic treatment such as a combination of methotrexate or cyclosporine and phototherapy, whereas those with the most severe form of psoriasis may be treated with biotherapies.

Fenoldopam mesylate, chemically 6-chloro-2,3,4,5-tetrahydro-1-(4-hydroxyphenyl)-1H-3-benzazepine-7,8-diol, methanesulfonate, is a highly selective agonist for the dopamine D1 receptor (D1R), which has been used in the clinic by intravenous administration for its vasodilatory actions mainly in the treatment of severe hypertension. The minimal blood levels of Fenoldopam that have some systemic vasodilatory effect is in the range of between 1 to 10 ng/mL (FDA Clinical Pharmacology & Biopharmaceutics Review, DA 19922, Corlopam®).

PCT Publication No. WO 2018/042352 disclosed herein by reference, relates to a method of treating skin disorders, preferably T-cell mediated auto-immune skin inflammatory disorders by topically administering a therapeutically effective amount of Fenoldopam or its pharmaceutically acceptable salts. Disorders reported in PCT Publication No. WO 2018/042352 include D1 receptor-mediated skin disorders, e.g., psoriasis, atopic dermatitis, alopecia, and vitiligo.

Fenoldopam exhibits both solubility and stability challenges, especially in aqueous formulations. Fenoldopam mesylate is only sparingly soluble in water, ethanol and methanol, and is soluble in propylene glycol. Moreover, the pH of the formulation is known to affect its stability.

Corlopam® for intravenous injection contains Fenoldopam mesylate, citric acid, propylene glycol, sodium citrate dihydrate and sodium metabisulfite in sterile aqueous solution. To keep the product stable in the presence of water, its pH is acidic in the range of 2.8-3.8. Moreover, the diluted solutions should be discarded after 4 hours at room temperature or 24 hours at refrigerated temperature, emphasizing the stability issues of Fenoldopam in the presence of water.

U.S. Pat. Nos. 6,699,497 and 6,960,353, directed to the transdermal administration of Fenoldopam for the treatment of hypertension, disclose the stability issue of Fenoldopam and state that when using aqueous formulations, it is preferable to maintain the pH at less than about 5.5, more preferably between about pH 2-4.5, in order to provide a stable Fenoldopam formulation. PCT Publication No. WO 2018/042352 experimentally demonstrated that maintaining the pH below 4 protected Fenoldopam from being degraded.

SUMMARY OF THE INVENTION

The present disclosure is directed to a topical composition of Fenoldopam comprising about 0.1% to about 5% by weight of Fenoldopam or a pharmaceutically acceptable salt thereof, at least one polyacrylamide-type gelling agent, at least one cellulose-type gelling agent, and at least one solvent, wherein the Fenoldopam is substantially solubilized in the composition, and wherein the composition is physically and chemically stable for at least one month at 25° C. and 60% relative humidity.

Applicants of the present disclosure successfully developed topical compositions of Fenoldopam which exhibit important features necessary for effective topical pharmaceutical compositions. Specifically, to achieve a topically effective composition, it is desirable that the active pharmaceutical ingredient (API) will be solubilized in the composition in order to enhance penetration into the skin, and that the composition will have a pH value in the range of 4-6 to avoid skin irritation. Furthermore, the composition should be physically and chemically stable during storage. Unexpectedly, Applicants of the present disclosure were able to overcome the solubility and stability challenges of Fenoldopam as the active ingredient and to develop topical compositions comprising a therapeutically effective amount of Fenoldopam with at least 0.1% by weight of Fenoldopam.

Applicants of the present disclosure unexpectedly discovered that the physical and chemical stability of a topical composition comprising a therapeutically effective amount of Fenoldopam may be achieved by using a combination of at least one polyacrylamide-type gelling agent and at least one cellulose-type gelling agent. Unexpectedly, the combination of these gelling agents improves not only the physical stability of the composition but also the chemical stability of Fenoldopam over a period of at least twelve months.

Moreover, Applicants of the present disclosure unexpectedly discovered that the presence of a combination of at least one polyacrylamide-type gelling agent and at least one cellulose-type gelling agent in the composition maintains the physical and chemical stability and the solubility of Fenoldopam even in water-containing compositions and in pH values equal to or higher than 4, which is in the range suitable for topical administration.

Furthermore, the topical compositions of the present disclosure enable the penetration of Fenoldopam into the skin, making it therapeutically effective for the treatment of skin disorders.

According to the present disclosure, the topical Fenoldopam compositions comprise a therapeutically effective amount of Fenoldopam or its salt and a combination of: (a)

at least one polyacrylamide-type gelling agent; (b) at least one cellulose-type gelling agent and (c) at least one solvent.

In some embodiments, the compositions comprise Fenoldopam in its base form.

In some embodiments, the compositions comprise Fenoldopam salt. In a preferred embodiment, the Fenoldopam salt is Fenoldopam mesylate.

In some embodiments, the therapeutic effective amount of Fenoldopam in the composition is from about 0.1% to about 5% by weight of the composition. In some embodiments, the effective amount of Fenoldopam in the composition is from about 0.5% to about 4% by weight of the composition. In a preferred embodiment, the effective amount of Fenoldopam in the composition is from about 1% to about 3% by weight of the composition.

According to some embodiments of the disclosure, the topical compositions comprise at least one polyacrylamide-type gelling agent. In some embodiments, the polyacrylamide-type gelling agent is selected from acrylamide/sodium acryloyldimethyl taurate copolymer/isohexadecane/polysorbate 80 mixture (Sepineo™ P600), polyacrylamide/C13-14 isoparaffin/laureth-7 mixture (Sepigel™ 305), hydroxyethyl acrylate/sodium acryloyldimethyl taurate copolymer mixture (Sepinov™ EMT 10) and hydroxyethyl acrylate/sodium acryloyldimethyl taurate copolymer (Sepineo™ DERM). In a preferred embodiment, the polyacrylamide-type gelling agent is acrylamide/sodium acryloyldimethyl taurate copolymer/isohexadecane/polysorbate 80 mixture (Sepineo™ P600).

According to various embodiments of the disclosure, the topical compositions further comprise a cellulose-type gelling agent. In a preferred embodiment, the cellulose-type gelling agent is hydroxypropyl cellulose. In some embodiments, the cellulose-type gelling agent is selected from ethyl cellulose, methyl cellulose, hydroxyethyl cellulose, hydroxypropyl cellulose (Klucel™) hydroxypropyl methylcelluloses, hydroxybutyl methylcellulose, carboxymethylcellulose, and combinations thereof.

According to a preferred embodiment, the topical compositions comprise a combination of Sepineo™ P600 and hydroxypropyl cellulose.

According to some embodiments of the disclosure, the amount of the polyacrylamide-type gelling agents in the composition is from about 1% to about 5% by weight of the composition.

According to some embodiments of the disclosure, the amount of the cellulose-type gelling agents in the composition is from about 1% to about 5% by weight of the composition.

According to some embodiments of the disclosure, the topical compositions further comprise at least one co-solvent. According to additional embodiments, the compositions comprise at least one solvent and at least one co-solvent. In some embodiments the solvent is selected from propylene glycol, dimethyl isosorbide, glycerin, ethanol, polyethylene glycol, hexylene glycol, diethylene glycol monoethyl ether and combinations thereof. In some embodiments, the co-solvent is selected from propylene glycol, dimethyl isosorbide, glycerin, ethanol, polyethylene glycol, hexylene glycol, diethylene glycol monoethyl ether and combinations thereof.

In additional embodiments, the topical compositions further comprise at least one emollient. In some embodiments, the emollient is selected from PPG-15 stearyl ether, PPG-12/SDMI copolymer, isostearic acid, cetearyl octanoate, cyclomethicone, propylene glycol, octyldodecanol, glycerol, diisopropyl adipate and combinations thereof.

According to the present disclosure, the Fenoldopam is substantially solubilized in the compositions. In some embodiments, at least about 80% of the Fenoldopam is solubilized in the compositions. In some embodiments, at least about 90% of the Fenoldopam is solubilized in the compositions. In some embodiments, at least about 95% of the Fenoldopam is solubilized in the compositions. In some embodiments, about 100% of Fenoldopam is solubilized in the compositions.

In some embodiments, the weight % of Fenoldopam in the composition is reduced by less than about 10% after one month at 25° C. and 60% relative humidity. In some embodiments, the weight of Fenoldopam in the composition is reduced by less than about 10% after 6 months at 25° C. and 60% relative humidity. In some embodiments, the weight/0 of Fenoldopam in the composition is reduced by less than about 10% after 9 months at 25° C. and 60% relative humidity. In some embodiments, the weight percentage of Fenoldopam in the composition is between 90%-110% of the label claim of Fenoldopam for at least one month. In some embodiments, the weight percentage of Fenoldopam in the composition is between 90%-110% of the label claim of Fenoldopam for at least six months. In some embodiments, the weight percentage of Fenoldopam in the composition is between 90%-110% of the label claim of Fenoldopam for at least 12 months, 18 months, 24 months, 30 months, or 36 months.

In some embodiments, the composition comprises less than about 0.2% by weight impurity B after at least one month at 25° C. and 60% relative humidity. In some embodiments, the composition comprises less than about 0.2% by weight impurity B after at least six months at 25° C. and 60% relative humidity. In some embodiments, the composition comprises less than about 0.2% by weight impurity B after at least nine months, 12 months, 18 months, 24 months, 30 months, or 36 months at 25° C. and 60% relative humidity. In some embodiments, the composition is homogenous for at least one month at 25° C. and 60% relative humidity. In some embodiments, the composition is homogenous for at least six months at 25° C. and 60% relative humidity. In some embodiments, the composition is homogenous for at least nine months, 12 months, 18 months, 24 months, 30 months, or 36 months at 25° C. and 60% relative humidity.

In some embodiments, the composition is a semisolid topical dosage form or a liquid topical dosage form. In some embodiments, the dosage form is an ointment, cream, lotion, gel, spray, foam, cloth, patch, wipe, or pad.

According to various embodiments of the disclosure, the topical Fenoldopam compositions can be an anhydrous composition or a water-containing composition.

In some embodiments, the topical composition is an anhydrous composition. According to a preferred embodiment, the anhydrous composition is an anhydrous gel.

In some embodiments, the topical composition further comprises water. According to a preferred embodiment, the water-containing composition is an O/W emulsion. In some embodiments the O/W emulsion is in the form of a cream.

In some embodiments, the water-containing compositions comprise at least one pH adjusting agent in order to maintain a pH level which is suitable for topical administration. In some embodiments, the pH adjusting agent is selected from sodium hydroxide, trolamine, citric acid, citrate buffer, phosphate buffer and carbonate buffer.

In some embodiments the water-containing composition has a pH range from about 3.5 to about 6.0, more preferably from about 4.0 to about 5.0. In some embodiments, the pH of the composition is about 4 to about 5 after at least one month at 25° C. and 60% relative humidity. In some embodiments, the pH of the composition is about 4 to about 5 after at least six months at 25° C. and 60% relative humidity.

In some embodiments, the topical compositions further comprise additional excipients including for example, preservatives, penetration enhancers, stabilizers, viscosity-increasing agents, thickeners, foaming agents, chelating agents or antioxidants.

According to the present disclosure, the Fenoldopam topical compositions are both physically and chemically stable for up to 12 months at room temperature conditions (25° C. and 60% relative humidity).

According to the present disclosure, the Fenoldopam topical compositions are both physically and chemically stable for at least three months at accelerated conditions (40° C. and 75% relative humidity).

According to additional embodiments, chemical stability of the compositions is obtained when the drug assay value expressed as % of Fenoldopam by weight is reduced by maximum of 10% throughout the specified period, and the level of impurity B is less than about 0.2% throughout the period. In some embodiments, the specified period is one month, three months, six months, nine months, 12 months, 18 months, 24 months, 30 months, or 36 months.

According to additional embodiments, chemical stability of the compositions is obtained when the weight percentage of Fenoldopam is between 90%-110% of the label claim of Fenoldopam for a specific time period. In some embodiments, the specific period is one month, three months, six months, nine months, 12 months, 18 months, 24 months, 30 months, or 36 months.

According to some embodiments, the physical stability of the compositions is determined by maintaining consistent macroscopic and microscopic appearance, pH level and viscosity of the composition throughout a period of at least one month, three months, six months, nine months, 12 months, 18 months, 24 months, 30 months, or 36 months.

According to additional embodiments, the physical stability of the compositions is determined by achieving homogenous appearance and absence of phase separation for a period of at least one month, three months, six months, nine months, 12 months, 18 months, 24 months, 30 months, or 36 months. In a further embodiment, the stability of the compositions is determined by achieving stable pH in the range of from about 4 to about 5 for a period of at least one month, three months, six months, nine months, 12 months, 18 months, 24 months, 30 months, or 36 months.

According to additional embodiments of the disclosure, the Fenoldopam topical compositions of the disclosure are used for the treatment of skin disorders. In some embodiments the skin disorders are T-cell mediated immune inflammatory disorders. In some embodiments the skin disorders are D1 receptor-mediated skin disorders.

According to additional embodiments, the skin disorders are selected from psoriasis, atopic dermatitis, alopecia, acne, rosacea and vitiligo. In a preferred embodiment, the skin disorder is psoriasis or atopic dermatitis. More preferably, the skin disorder is psoriasis.

In some embodiments, the disclosure is directed to a method of treating a D1 receptor-mediated skin disorder in a subject in need thereof, the method comprising topically administering the composition to an affected skin area of the subject, wherein the D1 receptor-mediated skin disorder is selected from psoriasis or atopic dermatitis.

BRIEF DESCRIPTION OF THE DRAWINGS

FIG. 1 shows Inflammatory markers of the psoriatic xenotransplants. All treated groups versus the vehicle-treated groups—p<0.05.

DETAILED DESCRIPTION OF THE INVENTION

The present disclosure is directed to physically and chemically stable topical compositions of Fenoldopam comprising from about 0.1% to about 5% by weight of Fenoldopam or a pharmaceutically acceptable salt thereof and a combination of: (a) at least one polyacrylamide-type gelling agent; (b) at least one cellulose-type gelling agent; and (c) at least one solvent, wherein the Fenoldopam is substantially solubilized in the composition and wherein the composition is stable for at least one month and is suitable for topical application for the efficient treatment of skin disorders.

Unless otherwise specified, the term "Fenoldopam" as used herein can include the base form of Fenoldopam, as well as a pharmaceutically acceptable salt, hydrate or solvate of Fenoldopam. In some embodiments, the composition comprises Fenoldopam in its base form. In some embodiments, the composition comprises a pharmaceutically acceptable salt, hydrate or solvate of Fenoldopam. In some embodiments, the composition comprises a Fenoldopam pharmaceutically acceptable salt.

In some embodiments, the Fenoldopam salt includes, but is not limited to, a hydrochloride, a hydrobromide or a mesylate salt. In some embodiments, the Fenoldopam salt is Fenoldopam mesylate.

In some embodiments, the composition comprises racemic Fenoldopam. In other embodiments, the composition comprises R-Fenoldopam.

In some embodiments, Fenoldopam in the composition is from about 0.1% to about 5%, by weight of the composition. In some embodiments, Fenoldopam in the composition is from about 0.5% to about 5%, by weight of the composition. In some embodiments, the Fenoldopam in the composition is from about 0.5% to about 4% by weight of the composition. In some embodiments, the Fenoldopam in the composition is from about 1% to about 3% by weight of the composition.

In some embodiments, Fenoldopam salt in the composition is from about 0.1% to about 5%, by weight of the composition. In some embodiments, Fenoldopam salt in the composition is from about 0.5% to about 5%, by weight of the composition. In some embodiments, the Fenoldopam salt in the composition is from about 0.5% to about 4% by weight of the composition. In some embodiments, the Fenoldopam salt in the composition is from about 1% to about 3% by weight of the composition.

In some embodiments, Fenoldopam mesylate in the composition is from about 0.1% to about 5% by weight of the composition. In some embodiments, Fenoldopam mesylate in the composition is from about 0.5% to about 5% by weight of the composition. In some embodiments, the Fenoldopam mesylate in the composition is from about 0.5% to about 4% by weight of the composition. In some embodiments, the Fenoldopam mesylate in the composition is from about 1% to about 3% by weight of the composition.

According to one embodiment of the present disclosure, the Fenoldopam topical composition is physically stable for a period of at least one month at room temperature. According to other embodiments, the Fenoldopam topical composition is physically stable for a period of at least 3 months, at least 6 months, at least 12 months, at least 18 months, at least 24 months, at least 30 months, or at least 36 months at room temperature.

According to one embodiment of the present disclosure, the Fenoldopam topical composition is chemically stable for a period of at least one month at room temperature. According to other embodiments, the Fenoldopam topical composition is chemically stable for a period of at least 3 months, at least 6 months, at least 12 months, at least 18 months, at least 24 months, at least 30 months, or at least 36 months at room temperature.

According to one embodiment of the present disclosure, the Fenoldopam topical composition is both physically and chemically stable for up to twelve months at room temperature. According to other embodiments, the Fenoldopam topical compositions are both physically and chemically stable for a period of at least 3 months, at least 6 months, at least 12 months, at least 18 months, at least 24 months, at least 30 months, or at least 36 months at room temperature.

According to additional embodiments of the present disclosure, the Fenoldopam topical composition is physically stable for a period of at least one month, at least 3 months or at least 6 months at accelerated conditions. According to additional embodiments of the present disclosure, the Fenoldopam topical composition is chemically stable for a period of at least one month, at least 3 months or at least 6 months at accelerated conditions. According to additional embodiments of the present disclosure, the Fenoldopam topical compositions are both physically and chemically stable for a period of at least one month, at least 3 months, at least 6 months, or at least 9 months at accelerated conditions.

The term "stable" as used herein refers to chemical stability of the active agent in the topical composition and/or physical stability of the composition over a specific period of time.

The term "physical stability" as used herein refers to maintaining consistency in the macroscopic and microscopic appearance, including but not limited to, parameters such as color, homogeneity, lack of phase separation, absence of crystals and constant droplet size, as well as in characteristics including pH and viscosity or spreadability of the composition throughout a specific period of time.

The term "chemically stable topical composition" as used herein can refer to topical composition in which the weight percent of Fenoldopam in the composition is reduced by less than about 10% after one month at 25° C. and 60% humidity, or is reduced by less than about 10% after six months at 25° C. and 60% humidity, or is reduced by less than about 10% after nine months at 25° C. and 60% humidity. In some embodiments, the term "chemically stable topical composition" as used herein can refer to topical composition in which the weight percent of Fenoldopam in the composition is reduced by about 0.01% to about 10%, about 0.1% to about 5%, about 1% to about 5% after one month at 25° C. and 60% humidity. In some embodiments, the term "chemically stable topical composition" as used herein can refer to topical composition in which the weight percent of Fenoldopam in the composition is reduced by less than about 4.5%, less than about 4%, less than about 3.5%, less than about 3%, less than about 2% or less than about 1% after one month at 25° C. and 60% humidity. In some embodiments, the term "chemically stable topical composition" as used herein can refer to topical composition in which the weight percent of Fenoldopam in the composition is reduced by about 0.01% to about 10%, about 0.1% to about 5%, about 1% to about 5% after six months at 25° C. and 60% humidity. In some embodiments, the term "chemically stable topical composition" as used herein can refer to topical composition in which the weight percent of Fenoldopam in the composition is reduced by less than about 4.5%, less than about 4%, less than about 3.5%, less than about 3%, less than about 2% or less than about 1% after six months at 25° C. and 60% humidity.

In some embodiments, chemical stability of the compositions is obtained when the weight percentage of Fenoldopam is between 90%-110% of the label claim of Fenoldopam for a specific time period. In some embodiments, the specific period is one month. In some embodiments, the specific period is three months, six months or nine months. The term "label claim" is the indicated weight percentage of the active ingredient, e.g., Fenoldopam, associated with a product comprising the composition of the present disclosure. Thus, e.g., a product having a label claim of "2% Fenoldopam composition" would have 1.8%-2.2% by weight (i.e., 90%-110%) Fenoldopam at T=0 and for a specific period of time. In some embodiments, chemical stability of the compositions is obtained when the weight percentage of Fenoldopam is between 90%-110% of the label claim of Fenoldopam for one month at 25° C. and 60% humidity. In some embodiments, chemical stability of the compositions is obtained when the weight percentage of Fenoldopam is between 90%-110% of the label claim of Fenoldopam for one month at 40° C. and 75% relative humidity. In some embodiments, chemical stability of the compositions is obtained when the weight percentage of Fenoldopam is between 90%-110% of the label claim of Fenoldopam for six months at 25° C. and 60% humidity. In some embodiments, chemical stability of the compositions is obtained when the weight percentage of Fenoldopam is between 90%-110% of the label claim of Fenoldopam for six months at 40° C. and 75% relative humidity.

The term "chemically stable topical composition" as used herein can refer to topical composition in which the composition comprises less than about 0.2% by weight impurity B after one month at 25° C. and 60% humidity. In some embodiments, the term "chemically stable topical composition" as used herein can refer to topical composition in which the composition comprises less than about 1%, less than about 0.1%, less than about 0.05% or less than 0.02% by weight impurity B after one month at 25° C. and 60% humidity. In some embodiments, the term "chemically stable topical composition" as used herein can refer to topical composition in which the composition comprises less than about 1%, less than about 0.1%, less than about 0.05% or less than 0.02% by weight impurity B after six months at 25° C. and 60% humidity.

The term "chemically stable topical composition" as used herein can refer to topical composition in which the composition comprises less than about 1% of any individual unknown impurity after one month at 25° C. and 60% humidity. The term "chemically stable topical composition" as used herein can refer to topical composition in which the composition comprises less than about 1% of any individual unknown impurity after six months at 25° C. and 60% humidity. In some embodiments, the term "chemically stable topical composition" as used herein can refer to topical composition in which the composition comprises less than about 0.5% of any individual unknown impurity after one month at 25° C. and 60% humidity. In some embodiments, the term "chemically stable topical composition" as used herein can refer to topical composition in which the composition comprises less than about 0.5% of any individual unknown impurity after six months at 25° C. and 60% humidity.

The term "anhydrous composition" as used herein can refer to topical composition which contains less than 1% by weight of water, e.g., less than 0.5%, less than 0.2% or less than 0.1% by weight water.

In some embodiments, the term "chemically stable topical composition" as used herein can refer to topical composition in which the weight percent of Fenoldopam in the composition is reduced by less than about 10%, e.g., less than about 5%, and the composition comprises less than about 0.2% by weight impurity B after one month at 25° C. and 60% humidity. The chemical and physical stability parameters are evaluated at 25° C. and 60% relative humidity (referred as "RT conditions"), intermediate (INT) conditions (30° C., 65% humidity), or 40° C. and 75% relative humidity (referred as "accelerated (ACC) conditions"), for a specific duration of 1, 3, 6, 12, 18, or 24 months.

The terms "composition" and "formulation" are interchangeably used.

The term "assay" as used herein refers to the determination of the drug content in the composition (i.e. "drug assay") by a specific analytical procedure such as HPLC. The drug product needs to contain the required amount of drug substance, and the assay is presented as percentage from the drug content at T=0. The drug assay is an indication for the stability of the composition.

The term "impurity" can be also referred to as "related compound" (RC). These can be known or unknown impurities of the drug substance. Fenoldopam mesylate related compound B or impurity B (ImpB) as referred herein is 2,3,4,5-Tetrahydro-1-(4-hydroxyphenyl)-1H-3-benzazepine-7,8-diol methanesulfonate salt (Deschloro-Fenoldopam mesylate) and is a known related compound of Fenoldopam mesylate.

According to some embodiments of the present disclosure, the chemical stability of the compositions is determined by drug assay values which are reduced by less than 10% relative to the initial assay value. According to some embodiments of the present disclosure, the chemical stability of the compositions is determined by drug assay values which are reduced by less than 5% relative to the initial assay value.

According to additional embodiments, the chemical stability is further determined by impurity B levels which are less than about 1.0% throughout a period of at least one month, less than about 0.75% throughout a period of at least one month, or less than about 0.5% throughout a period of at least one month. In some embodiments, the chemical stability is further determined by impurity B levels which are less than about 1.0% throughout a period of at least six months, less than about 0.75% throughout a period of at least six months, or less than about 0.5% throughout a period of at least six months. More preferably, the chemical stability is further determined by impurity B levels which are less than about 0.2% throughout a period of at least one month.

According to other embodiments, the chemical stability is further determined by any individual unknown impurity levels which are less than about 1.0% throughout a period of at least one month, less than about 0.75% throughout a period of at least one month, or less than about 0.5% throughout a period of at least one month. In some embodiments, the chemical stability is further determined by any individual unknown impurity levels which are less than about 1.0% throughout a period of at least six months, less than about 0.75% throughout a period of at least six months, or less than about 0.5% throughout a period of at least six months. More preferably, the chemical stability is further determined by any individual unknown degradation impurity levels which are less than about 0.2% throughout a period of at least one month.

According to yet additional embodiments, the chemical stability is further determined by total impurity levels of less than about 10%, less than about 5%, less than about 4%, less than about 3%, less than about 2%, or less than about 1% throughout a period of at least one month. In some embodiments, the chemical stability is further determined by total impurity levels of less than about 10%, less than about 5%, less than about 4%, less than about 3%, less than about 2%, or less than about 1% throughout a period of at least six months.

In some embodiments, the chemical stability of the compositions is obtained wherein the weight % of Fenoldopam in the composition is reduced by less than about 5% for a specific period, and the level of impurity B is less than about 0.2% for a specific period. In some embodiments, the specific period is one month. In some embodiments, the specific period is three months, six months nine months, 12 months, 18 months, 24 months, 30 months or 36 months.

According to additional embodiments, the physical stability of the composition is determined by maintaining homogenous appearance and/or absence of phase separation for at least one month. In a further embodiment the pH of the composition is about 4 to about 5 for at least one month.

In some embodiments, the disclosure provides topical compositions comprising a therapeutically effective amount of Fenoldopam or pharmaceutically acceptable salt thereof, and (a) at least one polyacrylamide-type gelling agent; (b) at least one cellulose-type gelling agent and (c) at least one solvent.

According to various embodiments of the disclosure, the topical composition comprises at least one polyacrylamide-type gelling agent. Examples of gelling agents from the polyacrylamide type include, but are not limited to, acrylamide/sodium acryloyldimethyl taurate copolymer/isohexadecane/polysorbate 80 mixture (Sepineo™ P600 or Simulgel™ 600), polyacrylamide/C13-14 isoparaffin/laureth-7 mixture (Sepigel™ 305), hydroxyethyl acrylate/sodium acryloyldimethyl taurate copolymer mixture (Sepinov™ EMT 10) and hydroxyethyl acrylate/sodium acryloyldimethyl taurate copolymer (Sepineo™ DERM). In some embodiments, the gelling agent is Sepineo™ P600.

According to various embodiments of the disclosure, the topical composition further comprises at least one cellulose-type gelling agent. Examples of gelling agents which are celluloses include, but are not limited to, alkyl celluloses such as ethyl celluloses and methyl celluloses, hydroxyalkyl celluloses such as hydroxyethyl cellulose and hydroxypropyl cellulose (Klucel™) hydroxyalkyl alkyl celluloses such as hydroxypropyl methylcelluloses and hydroxy butyl methylcelluloses, and carboxyalkyl cellulose such as carboxymethylcellulose. In some embodiments, the cellulose-type gelling agent is hydroxypropyl cellulose.

According to a preferred embodiment, the topical compositions comprise Sepineo™ P600 and hydroxypropyl cellulose.

According to some embodiments of the disclosure, the amount of the polyacrylamide-type gelling agent in the composition is from about 1% to about 5% by weight of the composition, or about 1%, about 2%, about 3%, about 4% or about 5% by weight of the composition.

According to some embodiments of the disclosure, the amount of each of the cellulose-type gelling agent in the composition is about 1% to about 5% by weight of the composition, or about 1%, about 2%, about 3%, about 4% or about 5% by weight of the composition.

The gelling agents as referred herein can also be referred to as emulsifying agents, thickening agents or viscosity-increasing agents.

Sepineo™ P600 is a concentrated dispersion of acrylamide/sodium acryloyldimethyl taurate copolymer in isohexadecane and polysorbate 80. The surprising ability of a polyacrylamide-type gelling agent such as Sepineo™ P600 to chemically stabilize Fenoldopam in the topical compositions of the disclosure is demonstrated in the present disclosure.

Without being bound to any specific theory, it is suggested that similarly to the mesylate, the acryloyldimethyl taurate can form a salt with Fenoldopam due to the sulfate group of the molecule. Forming a salt with Fenoldopam can lead to the stabilization of the Fenoldopam in the composition in the presence of Sepineo™ P600.

According to some embodiments of the disclosure, the topical composition further comprises at least one co-solvent.

Suitable solvents include, but are not limited to, propylene glycol, dimethyl isosorbide, glycerin, ethanol, polyethylene glycols (PEGs), hexylene glycol, diethylene glycol monoethyl ether and any combination thereof.

Suitable co-solvents include, but are not limited to, propylene glycol, dimethyl isosorbide, glycerin, ethanol, polyethylene glycols (PEGs), hexylene glycol, diethylene glycol monoethyl ether and any combination thereof.

In some embodiments, the solvent and cosolvent are the same. In some embodiments, the solvent and cosolvent are different.

According to some embodiments of the disclosure, the Fenoldopam is substantially solubilized in the composition. In some embodiments, at least about 80% of the Fenoldopam is solubilized in the composition. In some embodiments, at least about 90% of the Fenoldopam is solubilized in the composition. In some embodiments, at least about 95% of the Fenoldopam is solubilized in the composition. In some embodiments, about 100% of Fenoldopam is solubilized in the composition.

In additional embodiments, the topical compositions further comprise at least one emollient.

Non-limiting examples of emollients include PPG-15 stearyl ether, PPG-12/SDMI copolymer, isostearic acid, cetearyl octanoate, cyclomethicone, propylene glycol, octyldodecanol, glycerol, diisopropyl adipate and mixture thereof. In some embodiments, the emollients are PPG-15 stearyl ether and isostearic acid.

In some embodiments, the emollients are about 10% to about 35% by weight of the composition, about 10% to about 30% by weight of the composition, or about 10% to about 25% by weight of the composition.

In some embodiments, the compositions further comprise at least one preservative.

Suitable preservatives include, but are not limited to, benzoic acid and its salts and esters, benzyl alcohol, urea derivatives such as diazolidinyl urea, imidazolidinyl urea, and DMDM hydantoin, sorbic acid and its salts, and the like. Preservatives employed solely for that purpose will generally form 1% (w/w) or less of the final topical formulation. In some embodiments, the preservative is sorbic acid or benzoic acid.

In some embodiments, the topical composition further comprises additional excipients including for example, penetration enhancers, stabilizers, viscosity-increasing agents, thickeners, foaming agents, chelating agents or antioxidants.

Suitable penetration enhancers include, but are not limited to, polyols and esters, including polyethylene glycol, polyethylene glycol monolaurate, and butanediol; ethers, including diethylene glycol monoethyl ether (e.g., Transcutol. P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; and any mixtures thereof.

Suitable thickening agents include polyquaternium-10, Sepino™ P600, PEG 120 methyl glucose dioleate, sodium alginate, gum arabic, cellulose derivatives, such as methylcellulose, hydroxymethylcellulose, hydroxyethylcellulose, hydroxylpropylcellulose or hydroxypropylmethylcellulose, guar gum or its derivatives, xanthan gum, or combinations thereof.

Examples of water-soluble antioxidants include thiols such as thioglycerol, thiosorbitol, thiourea, thioglycolic acid, and cysteine, and the like. Examples of oil-soluble antioxidants include BHT (butylated hydroxytoluene), BHA (butylated hydroxyanisole), tocopherol (vitamin E), tocopheryl acetate, ascorbyl palmitate, hydroquinone, di-tbutylhydroquinone, propyl gallate, and the like.

Optional chelating agents include, but are not limited to, EDTA (ethylenediaminetetraacetic acid) and its salts, for example disodium EDTA, trisodium NTA, etidronic acid and its salts, sodium dihydroxyethylglycinate, citric acid and its salts, and the like. Preferably, the chelating agent is EDTA or its salts.

Suitable colorants and fragrances will be a matter of choice, provided only that they should be compatible with the formulation.

Some of the excipient substances described above can have more than one function in a formulation. For example, a substance can be both a solvent and a penetration enhancer, or both a gelling agent and a thickener. The categorizations of materials described above are not to be construed as limiting or restricting in any manner.

In some embodiments, the composition of the present disclosure is a semisolid topical dosage form or a liquid topical dosage form. In some embodiments, the dosage form is an ointment, cream, lotion, gel, spray, or foam.

In some embodiments, the topical composition is an anhydrous composition. According to a preferred embodiment, the anhydrous composition comprises an anhydrous gel.

In specific embodiments, the anhydrous gel composition comprises: (a) Fenoldopam or a pharmaceutically acceptable salt thereof, preferably at an amount of about 1-3%; (b) at least one polyacrylamide-type gelling agent, preferably at an amount of about 1-5%; (c) at least one cellulose-type gelling agent, preferably at an amount of about 1-5%; (d) at least one solvent, preferably at an amount of about 30-50%; (e) at least one filler, preferably at an amount of about 20-40%; (f) at least one emollient, preferably at an amount of about 15-35%; and (g) at least one preservative, preferably at an amount of less than about 0.2%.

In some embodiments, the topical composition is a water-containing composition. According to a preferred embodiment, the water-containing composition is an oil-in-water, i.e., O/W, emulsion. In some embodiments the O/W emulsion is in the form of a cream.

In some embodiments, the water-containing composition further comprises at least one pH adjusting agent.

Suitable pH adjusting agents include, but are not limited to, sodium hydroxide, trolamine, citric acid, citrate buffer, phosphate buffer, carbonate buffer. In some embodiments, the pH adjusting agent is selected from trolamine or sodium hydroxide.

In some embodiments the water-containing composition has a pH range of about 3.5 to about 6.0, or about 4.0 to about 5.0.

In specific embodiments, the O/W emulsion composition comprises: (a) Fenoldopam or a pharmaceutically acceptable salt thereof, preferably at an amount of about 1-3%; (b) at least one polyacrylamide-type gelling agent, preferably at an amount of about 1-5%; (c) at least one cellulose-type gelling agent, preferably at an amount of about 1-5%; (d) at least one solvent, preferably at an amount of about 5-20%; (e) at least one co-solvent, preferably at an amount of about 5-15%; (f) at least one emollient, preferably at an amount of about 10-25%; (g) water, preferably at an amount of about 50-70%; (g) at least one preservative, preferably at an amount of less than about 0.2%; and optionally (i) a pH adjusting agent as needed.

An important feature of a topical composition is its ability to penetrate through the skin layers. The topical compositions of the present disclosure provide penetration of the active agent Fenoldopam into the skin.

According to embodiments of the disclosure, at least 0.01%, at least 0.1%, at least 0.5%, at least 1%, at least 2%, at least 3%, at least 4%, at least 5%, at least 6%, at least 7%, at least 8%, at least 9% or at least 10% of the applied Fenoldopam dose penetrates into the skin. In some embodiments, dose penetration is determined as exemplified by Example 3.

In yet another embodiment, the maximal systemic absorption of the topical Fenoldopam compositions is less than about 10 ng/ml in blood. In another embodiment, the maximal systemic absorption of the topical Fenoldopam compositions is less than about 5 ng/ml. In another embodiment, the maximal systemic absorption of the topical Fenoldopam compositions is less than about 2.5 ng/ml. In another embodiment, the maximal systemic absorption of the topical Fenoldopam compositions is less than about 1 ng/ml. In another embodiment, the maximal systemic absorption of the topical Fenoldopam compositions is less than about 0.5 ng/ml. In another embodiment, the maximal systemic absorption of the topical Fenoldopam compositions is less than about 0.1 ng/ml.

According to an additional embodiment, not more than 1%, not more than 0.5%, not more than 0.1% or not more than 0.05% of the applied Fenoldopam dose permeates through the skin into the receptor cell in a penetration/permeation human skin study.

According to additional embodiments of the disclosure, the Fenoldopam topical compositions are for the treatment of skin disorders. In some embodiments the skin disorders are T-cell mediated immune inflammatory disorders. In some embodiments the skin disorders are D1 receptor-mediated skin disorders.

According to additional embodiments, the skin disorders are selected from psoriasis, atopic dermatitis, alopecia, acne, rosacea and vitiligo.

Accordingly, the compositions are suitable for application to a subject having a skin disorder selected from psoriasis, atopic dermatitis, alopecia, acne, rosacea and vitiligo.

In a preferred embodiment the skin disorder is psoriasis or atopic dermatitis.

In some embodiments, the compositions of the present disclosure are administered in combination with at least one additional pharmaceutical agent useful for treating a D1 receptor-mediated skin disorder. In some embodiments, the Fenoldopam therapeutic agent and the at least one additional pharmaceutical agent are in the same pharmaceutical composition. In some embodiments, the at least one additional pharmaceutical agent is selected, for example, from corticosteroids, Vitamin A or D or analogs, tazarotene, salicylic acid, coal-tar and anti-pruritic agents.

In some embodiments, the topical compositions of the disclosure are administered in combination with an additional therapeutic treatment known to be effective in a D1 receptor-mediated skin disorder. In some embodiments, the additional therapeutic treatment is selected from phototherapy or systemic therapy including small-molecule drugs and biological agents.

According to an additional aspect, the present disclosure provides a method of treating a D1 receptor-mediated skin disorder in a subject in need thereof, the method comprising topically administering to the affected area of skin of the subject a therapeutically effective amount of a topical composition of Fenoldopam comprising a therapeutically effective amount of about 0.1% to about 5% by weight of Fenoldopam or a pharmaceutically acceptable salt thereof, at least one polyacrylamide-type gelling agent, at least one cellulose-type gelling agent and at least one solvent, wherein the Fenoldopam is substantially solubilized in the composition and wherein the composition is stable for a period of at least one month.

A "therapeutically effective amount" or "therapeutically effective amounts" means the amount that, when administered to a subject for treating a disease, is sufficient to effect treatment for that disease.

The term "treating" or "treatment" of a disease, as used herein, includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

In some embodiments, the present disclosure provides a process for preparing a physically and chemically stable topical formulation comprising Fenoldopam, wherein the topical formulation is an anhydrous gel or O/W emulsion.

In some embodiments, the process for preparing the O/W emulsion comprises adding the active ingredient to an aqueous phase prior to the formation of the emulsion with the oil phase.

In some embodiments, the process for preparing the O/W emulsion comprises forming an emulsion by mixing the aqueous phase with the oil phase, and adding the active ingredient to the emulsion.

In a preferred embodiment, the process for preparing the O/W emulsion comprises forming an emulsion by mixing the aqueous phase with the oil phase, and adding the active ingredient to the emulsion.

In some embodiments, the process for preparing the O/W emulsion is performed at room temperature (from about 15° C. to about 30° C.).

Having now generally described this invention, the same will be better understood by reference to the following Examples, which are provided herein solely for purposes of illustration only and are not intended to be limiting of the invention or any embodiment thereof, unless so specified.

All references cited herein, including patents, patent applications, papers, textbooks and the like, and the references cited therein, to the extent that they are not already, are hereby incorporated herein by reference in their entirety.

EXAMPLES

Example 1: Fenoldopam Anhydrous Formulations

Formulation 1:

| # | Ingredient | % |
|---|---|---|
| 1 | GELOT64 | 7.0 |
| 2 | Medium chain triglycerides | 20.0 |
| 3 | Hydrogenated Castor Oil | 2.0 |
| 4 | Mineral oil USP | 22.9 |
| 5 | Cetostearyl Alcohol | 11.0 |
| 6 | Shea butter | 2.0 |
| 7 | Glycerin | 20.0 |
| 8 | Propylene glycol | 15.0 |
| 9 | Fenoldopam Mesylate | 0.1 |

The formulation with GELOT64 was physically and chemically unstable. It was non-homogenous and the total impurity levels increased from 1.3% at T=0 to 21.6% after 3M in accelerated stability conditions (ACC) (Table 1). More specifically, an unknown impurity (UnK Imp 1 in table 1), related to degradation of the API, appeared in the composition after 3 months in accelerated conditions at very high levels (21.6% at 3M ACC).

TABLE 1

| | T = 0 | 2 weeks, 50° C. | 1M, ACC | 3M, ACC |
|---|---|---|---|---|
| % RC | | | | |
| UnK Imp 1 | ND | ND | ND | 21.6 |
| UnK Imp 2 | 1.3 | 3.6 | 12.95 | ND |
| Total Imp % | 1.3 | 3.6 | 12.95 | 21.6 |

\* ND—not detected

\*\* UnK Imp—unknown impurity. The unknown impurities are arbitrarily numbered in each table.

Formulation 2:

| # | Ingredient | % |
|---|---|---|
| 1 | PEG 400 NF | 48.0 |
| 2 | Propylene glycol | 19.9 |
| 3 | Glycerin USP | 20.0 |
| 4 | Polysorbate 80 | 10.0 |
| 6 | Sepineo ™ P600 | 1.5 |
| 7 | Carbopol 980 | 0.5 |
| 8 | Fenoldopam Mesylate | 0.1 |

Formulation 2 contains Sepineo and carbomer (carbopol) as gelling agents with 0.1% Fenoldopam. At low concentrations of Fenoldopam mesylate, such as 0.1%, the formulation with Sepineo and carbomer showed both chemical and physical stability. However, at high concentration of Fenoldopam, such as 1% or 2%, the physical stability of the formulation was impaired due to the formation of agglomerates.

Formulations 3A-3F: Formulations with Combination of Sepineo and Hydroxypropyl Cellulose and Between 0.5% to 3% Fenoldopam were Prepared and their Stability was Evaluated.

| # Ingredient | 3A | 3B | 3C | 3D | 3E | 3F |
|---|---|---|---|---|---|---|
| 1 Propylene glycol | 30.0-50.0 | 30.0-50.0 | 30.0-50.0 | 30.0-50.0 | 30.0-50.0 | 30.0-50.0 |
| 2 PEG 400 NF | 20.0-40.0 | 20.0-40.0 | 20.0-40.0 | 20.0-40.0 | 20.0-40.0 | 20.0-40.0 |
| 3 Glycerin USP | 10.0-25.0 | 10.0-25.0 | 10.0-25.0 | 10.0-25.0 | 10.0-25.0 | 10.0-25.0 |
| 4 PPG-15 Stearyl ether | 5.0-10.0 | 5.0-10.0 | 5.0-10.0 | 5.0-10.0 | 5.0-10.0 | 5.0-10.0 |
| 5 Hydroxypropyl Cellulose (Klucel ™) | 1.0 | 1.5 | 2.5 | 2.5 | 4.0 | 5.0 |
| 6 Sepineo ™ P600 | 1.5 | 1.5 | 1.5 | 1.5 | 1.5 | 1.5 |
| 7 Sorbic Acid | 0.0-0.2 | 0.0-0.2 | 0.0-0.2 | 0.0-0.2 | 0.0-0.2 | 0.0-0.2 |
| 8 Fenoldopam Mesylate | 0.5 | 1.0 | 1.0 | 2.0 | 2.0 | 3.0 |

In the presence of Sepineo™ P600 and hydroxypropyl cellulose no agglomerates were formed and the formulations were physically stable in a wide range of concentrations of Fenoldopam. Moreover, the combination of Sepineo™ P600 and hydroxypropyl cellulose surprisingly resulted in both physical stability and chemical stability of the composition with no significant change in Fenoldopam assay (98% at T=0 and 98.1% after 3 months in RT) and total impurity levels of less than 0.2% (0.16% at T=0 and 0.11% after 3 months in RT) after 3 months stability at RT (room temperature). Importantly, in the presence of hydroxypropyl cellulose and Sepineo™ P600, the levels of ImpB and any individual unknown impurity (UnK Imp) were less than 0.2%, even after 3 months at accelerated conditions (Table 2).

TABLE 2

Formulation 3 (based on prototype 3D)
(2% Fenoldopam mesylate)

|  | T = 0 | 1M, RT | 1M, ACC | 3M, RT | 3M, ACC |
|---|---|---|---|---|---|
| Appearance | Homogenous transparent gel | Homogenous transparent gel | Homogenous transparent gel | Homogenous transparent gel | Homogenous Transparent gel |
| % Fenoldopam Assay | 98 | 97.3 | 97.4 | 98.1 | 98.1 |
| % RC |  |  |  |  |  |
| ImpB | 0.09 | 0.11 | 0.11 | 0.11 | 0.13 |
| UnK Imp 1 | ND | 0.02 | 0.06 | ND | 0.18 |
| UnK Imp 2 | 0.07 | 0.03 | ND | ND | ND |
| UnK Imp 3 | ND | ND | 0.08 | ND | ND |
| UnK Imp 4 | ND | ND | 0.06 | ND | ND |
| UnK Imp 5 | ND | ND | ND | ND | 0.12 |
| UnK Imp 6 | ND | ND | ND | ND | 0.15 |
| Total Imp | 0.16 | 0.16 | 0.31 | 0.11 | 0.58 |
| Viscosity (cP) | 4828 | 5569 | 6697 | 6033 | 6253 |

\* ND—not detected
\*\* UnK Imp—unknown impurity. The unknown impurities are arbitrarily numbered in each table.

The table below represents different concentrations of Sepineo and its effect on stability. The levels of Sepineo™ P600 were increased and varied in the range of 1.0 to 5.0% (Formulations 4A-4F).
Formulations 4A-4F:

| # Ingredient | 4A | 4B | 4C | 4D | 4E | 4F |
|---|---|---|---|---|---|---|
| 1 Propylene glycol | 30.0-50.0 | 30.0-50.0 | 30.0-50.0 | 30.0-50.0 | 3550.0 | 30.0-50.0 |
| 2 PEG 400 NF | 20.0-40.0 | 20.0-40.0 | 20.0-40.0 | 20.0-40.0 | 20.0-40.0 | 20.0-40.0 |
| 3 Glycerin USP | 10.0-25.0 | 10.0-25.0 | 10.0-25.0 | 10.0-25.0 | 10.0-25.0 | 10.0-25.0 |
| 4 PPG-15 Stearyl ether | 5.0-10.0 | 5.0-10.0 | 5.0-10.0 | 5.0-10.0 | 5.0-10.0 | 5.0-10.0 |
| 5 Hydroxypropyl Cellulose (Klucel ™) | 1.0-5.0 | 1.0-5.0 | 1.0-5.0 | 1.0-5.0 | 1.0-5.0 | 1.0-5.0 |
| 6 Sepineo ™ P600 | 1.5 | 2.5 | 4.0 | 2.5 | 4.0 | 5.0 |
| 7 Sorbic Acid | 0.0-0.2 | 0.0-0.2 | 0.0-0.2 | 0.0-0.2 | 0.0-0.2 | 0.0-0.2 |
| 8 Fenoldopam Mesylate | 1.0 | 1.0 | 1.0 | 2.0 | 2.0 | 3.0 |

The stability of representative Formulations prepared based on prototype 4B (1% Fenoldopam) and 4D (2% Fenoldopam) was evaluated through at least one month period (Tables 3 and 4). The reduction in Fenoldopam assay was less than 5% after 1M in RT (96% at T=0 and 93.9 at 1M, RT; 97.1% at T=0 and 95.3% at 1M, RT for 1% and 2% Fenoldopam, respectively) and total impurity levels were the same or even decreased (0.9% at T=0 and 0.9% at 1M, RT and 0.93% at T=0 and 0.81 at 1M, for 1% and 2% Fenoldopam respectively). Importantly, impurity B levels did not change significantly throughout the stability period at both RT and accelerated conditions and were less than 0.2%, and any individual unknown impurity was less than 1%. Moreover, there was no prominent change in the viscosity of the formulation, further supporting the stability of the compositions.

TABLE 3

Formulation 4 (based on prototype 4B)
(1% Fenoldopam mesylate)

|  | T = 0 | 2 weeks, 50° C. | 1M, RT | 1M, ACC |
|---|---|---|---|---|
| Appearance | Homogenous gel | Homogenous gel | Homogenous gel | Homogenous gel |
| % Fenoldopam Assay | 96 | 95.3 | 93.9 | 93.2 |
| % RC |  |  |  |  |
| ImpB | 0.10 | 0.11 | 0.09 | 0.10 |
| UnK Imp 1 | ND | ND | 0.09 | 0.07 |
| UnK Imp 2 | ND | ND | 0.10 | 0.10 |
| UnK Imp 3 | ND | ND | 0.62 | 0.60 |
| UnK Imp 4 | 0.27 | 0.10 | ND | ND |
| UnK Imp 5 | ND | ND | ND | 0.07 |
| UnK Imp 6 | 0.47<sup>a</sup> | 0.64<sup>a</sup> | ND | ND |
| UnK Imp 7 | ND | ND | ND | 0.07 |
| UnK Imp 8 | 0.06 | 0.07 | ND | ND |
| UnK Imp 9 | ND | 0.06 | ND | ND |
| Total Imp | 0.90 | 0.98 | 0.90 | 1.01 |
| Viscosity (cP) | 18788 | 16882 | 19420 | 18686 |

\* ND—not detected
<sup>a</sup>unknown impurity which originally relates to the API source
\*\* UnK Imp—unknown impurity. The unknown impurities are arbitrarily numbered in each table.
\*\*\* 1M stability data is for formulation packed in aluminum tubes.

TABLE 4

Formulation 4 (based on prototype 4D)
(2% Fenoldopam mesylate)

|  | T = 0 | 2 weeks, 50° C. | 1M, RT | 1M, ACC |
|---|---|---|---|---|
| Appearance | Homogenous gel | Homogenous gel | Homogenous gel | Homogenous gel |
| % Fenoldopam Assay | 97.1 | 97.1 | 95.3 | 95.6 |
| % RC |  |  |  |  |
| ImpB | 0.09 | 0.12 | 0.09 | 0.09 |
| UnK Imp 1 | ND | ND | 0.10 | 0.10 |
| UnK Imp 2 | ND | ND | 0.62 | 0.62 |
| UnK Imp 3 | 0.10 | 0.08 | ND | ND |
| UnK Imp 4 | 0.63<sup>a</sup> | 0.63<sup>a</sup> | ND | ND |
| UnK Imp 5 | 0.11 | ND | ND | ND |
| Total Imp | 0.93 | 0.83 | 0.81 | 0.81 |
| Viscosity (cP) | 17170 | 15216 | 14228 | 15746 |

\* ND—not detected
<sup>a</sup>unknown impurity which originally relates to the API source
\*\* UnK Imp—unknown impurity. The unknown impurities are arbitrarily numbered in each table.
\*\*\* 1M stability data is for formulation packed in aluminum tubes.

The results unexpectedly demonstrate that the anhydrous gel formulations comprising both Sepineo™ P600 and a cellulose derivative are both chemically and physically stable. Specifically, the level of any unknown impurity was less than 1%, drug assay values were reduced by not more than 5% relative to the initial assay value, and the level of impurity B was less than about 0.2% by weight, following one month at 25° C. and 60% relative humidity. Moreover, these formulations of the current disclosure enable the solubilization of high concentrations of Fenoldopam, thus making it suitable for efficient topical application.

Example 2: Fenoldopam O/W Emulsion Formulations

Formulation 5:

| # | Ingredient | % |
|---|---|---|
| 1 | PPG-15 Stearyl ether | 8.00 |
| 2 | Medium Chain Triglycerides | 10.00 |
| 3 | Steareth-2 | 4.00 |
| 4 | Macrogol Stearyl ether | 4.00 |
| 5 | Propylene glycol | 8.00 |
| 6 | Fenoldopam Mesylate | 0.10 |
| 7 | Purified water | 65.9 |

Formulation 6:

| # | Ingredient | % |
|---|---|---|
| 1 | PPG-15 Stearyl ether | 8.00 |
| 2 | Medium Chain Triglycerides | 10.00 |
| 3 | Sepineo™ P600 | 3.00 |
| 4 | Propylene glycol | 8.00 |
| 5 | Fenoldopam Mesylate | 0.10 |
| 6 | Purified water | 70.90 |

Sepineo™ P600 unexpectedly improved the chemical stability of Fenoldopam in the O/W emulsion formulation, as reflected by the prominent decrease in the impurity levels of Fenoldopam mesylate from 38.56% total impurities to 6.36% after 6 months at accelerated stability conditions. Importantly, the levels of unknown Imp 1 which its formation is accelerated in the presence of water in the composition, decreased significantly with the addition of Sepineo™ P600 (from 30.22% to 4.48% after 6 months at accelerated stability conditions) (Table 5). However, further improvements in chemical stability were required in compositions with higher concentration of Fenoldopam.

TABLE 5

|  | 6 M, ACC Formulation 5 (No Sepineo™ P600) | 6 M, ACC Formulation 6 (With Sepineo™ P600) |
|---|---|---|
| % RC |  |  |
| UnK Imp 1 | 30.22 | 4.48 |
| Total Imp | 38.56 | 6.36 |
| pH | 4.17 | 4.6 |

\*\* UnK Imp—unknown impurity. The unknown impurities are arbitrarily numbered in each table.

Formulation 7:

| # | Ingredient | % |
|---|---|---|
| 1 | PPG-15 Stearyl ether | 8.00 |
| 2 | Medium-chain Triglycerides | 10.00 |
| 3 | Sepineo™ P600 | 3.00 |
| 4 | Propylene glycol | 8.00 |
| 5 | DMSO | 5.00 |
| 6 | Fenoldopam Mesylate | 2.00 |
| 7 | Phenoxyethanol | 1.00 |
| 6 | Purified water | 63.00 |

Formulation 7 was physically unstable with phase separation.

Formulation 8:

| # | Ingredient | % |
|---|---|---|
| 1 | Isostearic Acid | 20.00 |
| 2 | Medium-chain Triglycerides | 12.00 |
| 3 | SepineoTm ™ P600 | 3.00 |
| 4 | Fenoldopam Mesylate | 2.00 |
| 5 | Trolamine | 0.10 |
| 6 | Phenoxyethanol | 1.00 |
| 7 | Purified water | 61.90 |

Formulation 8 was physically unstable with many aggregates.

Formulations 9A-9I:

| # Ingredient | 9A | 9B | 9C | 9D | 9E | 9F | 9G | 9H | 9I |
|---|---|---|---|---|---|---|---|---|---|
| 1 Isostearic acid | 10.0-25.0 | 10.0-25.0 | 10.0-25.0 | 10.0-25.0 | 10.0-25.0 | 10.0-25.0 | 10.0-25.0 | 10.0-25.0 | 10.0-25.0 |
| 2 Propylene glycol | 5.0-20.0 | 5.0-20.0 | 5.0-20.0 | 5.0-20.0 | 5.0-20.0 | 5.0-20.0 | 5.0-20.0 | 5.0-20.0 | 5.0-20.0 |
| 3 Dimethyl Isosorbide | 5.0-15.0 | 5.0-15.0 | 5.0-15.0 | 5.0-15.0 | 5.0-15.0 | 5.0-15.0 | 5.0-15.0 | 5.0-15.0 | 5.0-15.0 |
| 4 Sepineo ™ P600 | 1.5 | 2.5 | 4.0 | 4.0 | 2.5 | 4.0 | 4.0 | 4.0 | 5.0 |
| 5 Hydroxypropyl Cellulose (Klucel ™) | 1.0 | 1.0 | 1.0 | 2.5 | 1.0 | 1.0 | 2.5 | 2.5 | 4.0 |
| 6 Sorbic acid | 0.0-0.2 | 0.0-0.2 | 0.0-0.2 | 0.0-0.2 | 0.0-0.2 | 0.0-0.2 | 0.0-0.2 | 0.0-0.2 | 0.0-0.2 |
| 7 Fenoldopam Mesylate | 0.5 | 1.0 | 1.0 | 1.0 | 2.0 | 2.0 | 2.0 | 3.0 | 3.0 |
| 8 Purified water | 50.0-70.0 | 50.0-70.0 | 50.0-70.0 | 50.0-70.0 | 50.0-70.0 | 50.0-70.0 | 50.0-70.0 | 50.0-70.0 | 50.0-70.0 |
| 9 pH adjusting agent | q. s. | q. s. | q. s. | q. s. | q. s. | q. s. | q. s. | q. s. | q. s. |

Formulations 9A-9I were prepared with a combination of Sepineo and hydroxypropyl cellulose in various concentrations and between 0.5% to 3% Fenoldopam. The stability of representative formulations was evaluated through at least 1 month period (Tables 6 and 7). The combination of Sepineo and hydroxypropyl cellulose unexpectedly improved the stability of the composition. The change in Fenoldopam assay was less than 5% after 1M in RT (97.8% at T=0 and 97.1 at 1M, RT; 98.8% at T=0 and 97.0% at 1M, RT for 1% and 2% Fenoldopam, respectively) and the levels of each impurity, including ImpB and any individual unknown degradation impurity were less than 0.2%. The emulsion was homogenous and there was no prominent change in the viscosity within each formulation, further supporting the stability of the compositions. Most importantly, the pH of the formulations at various concentrations of Fenoldopam did not change during stability and was maintained in the range of 4.1-4.2.

TABLE 6

Formulation 9 (based on prototype 9C) (1% Fenoldopam mesylate)

| Appearance | T = 0 Homogenous emulsion | 2 W, 50° C. Homogenous emulsion | 1 M, RT Homogenous emulsion | 1 M, ACC Homogenous emulsion |
|---|---|---|---|---|
| % Fenoldopam Assay % RC | 97.8 | 96.4 | 97.1 | 96.9 |
| ImpB | 0.11 | 0.15 | 0.10 | 0.12 |
| UnK Imp 1 | ND | 0.11 | ND | ND |
| UnK Imp 2 | ND | 0.02 | ND | ND |
| UnK Imp 3 | ND | ND | ND | 0.04 |
| Total Imp | 0.11 | 0.28 | 0.10 | 0.16 |
| Viscosity (cP) | 99064 | 86102 | Not tested | 88726 |
| pH | 4.18 | 4.11 | 4.2 | 4.1 |

\* ND—not detected
\*\* UnK Imp—unknown impurity. The unknown impurities are arbitrarily numbered in each table.
\*\*\* 1 M stability data is for formulation packed in aluminum tubes.

TABLE 7

Formulation 9 (based on prototype 9F) (2% Fenoldopam mesylate)

| Appearance | T = 0 Homogenous emulsion | 2 W, 50° C. Homogenous emulsion | 1 M, RT Homogenous emulsion | 1 M, ACC Homogenous emulsion |
|---|---|---|---|---|
| % Fenoldopam Assay % RC | 98.8 | 96.5 | 97 | 96.4 |
| ImpB | 0.13 | 0.18 | 0.13 | 0.16 |
| UnK Imp 1 | ND | 0.12 | ND | ND |
| UnK Imp 2 | ND | ND | ND | 0.04 |
| UnK Imp 3 | ND | ND | 0.18 | 0.17 |
| UnK Imp 4 | 0.05 | 0.17 | ND | ND |
| Total Imp | 0.18 | 0.47 | 0.31 | 0.37 |
| Viscosity (cP) | 5483 | 3308 | 4690 | 3426 |
| pH | 4.18 | 4.11 | 4.2 | 4.1 |

\* ND—not detected
\*\* UnK Imp—unknown impurity. The unknown impurities are arbitrarily numbered in each table.
\*\*\* 1 M stability data is for formulation packed in aluminum tubes.

The results unexpectedly demonstrate that the 01W emulsion formulations comprising both Sepineo™ P600 and a cellulose derivative are both chemically and physically stable. Specifically, the level of any unknown impurity was less than 1%, drug assay values were reduced by not more than 5% relative to the initial assay value, and the level of impurity B was less than about 0.2% by weight, following one month at 25° C. and 60% relative humidity. Moreover, the formulations of the current disclosure enable the solubilization of high concentrations of Fenoldopam while maintaining pH of 4-5, thus making it suitable for efficient topical application.

Example 3: Skin Penetration/Permeation Studies

The penetration/permeation model is a well-validated tool for the study of percutaneous absorption of topically applied drugs. The model uses excised human skin mounted in specially designed diffusion chambers that allow the skin to be maintained at a temperature and humidity that match real use conditions. The composition is applied to the surface of the skin and the penetration of the compound is measured by monitoring its rate of appearance in the skin layers, as well as the receptor solution flowing underneath the skin samples. Also, this in vitro system has the potential for carefully controlling many of the potential variables involved in topical application, like dosing volumes, humidity, temperature, drug stability, skin thickness, etc.

The dermatomed skin is positioned between the two halves of the diffusion cell with the stratum corneum facing the donor compartment allowing for drug application. The drug concentrations permeating across human skin and drug penetration within the different skin layers are measured.

To determine the penetration of Fenoldopam into the skin from the representative topical compositions, an in vitro penetration/permeation study was conducted using cadaver skin. The total amounts of Fenoldopam mesylate within the skin (penetration) and in the receptor cell (permeation) were analyzed.

The in vitro skin penetration/permeation studies were determined using vertical static Franz cells. Two pieces of excised heat-separated human skin from two different donors were used in this study. A total of 8 cells were used for each formulation with an average application dose of 13.36±1.79 mg/cm$^2$. Permeation study was performed with 0.1% v/v Phosphoric acid (0.1% PhA) as a receptor solution. The receptor solution was sampled at 7 time points in addition to $t_0$. After 48 hours, the skin surface was washed using pre-developed washing procedure and the skin surface was then tape stripped (≤10 time). Tape and skin extraction was performed with 5.0 mL of 0.1% Phosphoric acid and the samples were heated for 15 minutes at 65° C. Wash, tape, skin and permeation samples were analyzed to determined mass balance. All samples were analyzed with HPLC-UV. The electrical resistance of all skin samples was confirmed to be >20 kΩ as determined by the Transcutaneous Electrical resistance (TER) measurement which is done at 100 Hz.

4.1 Penetration/Permeation Results

Table 8 summarizes the percentage of Fenoldopam mesylate measured within the epidermis (defined as skin in the table) and within the stratum corneum (defined as tapes in the table), relative to the amount applied to the skin samples. Results are the average of two skin samples obtained from two different donors.

As revealed from Table 8, the percentage of Fenoldopam penetrated into the epidermis was higher than the percentage of Fenoldopam which remained in the stratum corneum in both the anhydrous gel and o/w formulations. Furthermore, the percentage of Fenoldopam which penetrated to the stratum corneum and to the epidermis was higher with 2% Fenoldopam compared to 1% Fenoldopam mainly in the o/w formulation.

TABLE 8

| | Anhydrous composition (Formulation 4) | | O/W composition (Formulation 9) | |
|---|---|---|---|---|
| % of the amount applied to the skin sample | 1% Fenoldopam mesylate (based on prototype 4B) | 2% Fenoldopam mesylate (based on prototype 4D) | 1% Fenoldopam mesylate (based on prototype 9C) | 2% Fenoldopam mesylate (based on prototype 9F) |
| Tapes | 0.78% | 1.33% | 0.98% | 3.08% |
| Skin | 3.34% | 3.12% | 2.32% | 8.54% |

Table 9 summarizes the cumulative percentage of Fenoldopam mesylate measured in the receptor cell relative to the amount applied to the skin samples following 24 and 48 hrs incubation. Results are the average of two skin samples obtained from two different donors.

As revealed from Table 9, less than 0.03% of the Fenoldopam dose applied on the skin permeated through the skin to the receptor cell in both anhydrous and o/w formulations.

TABLE 9

| | Anhydrous composition (Formulation 4) | | O/W composition (Formulation 9) | |
|---|---|---|---|---|
| % of the amount applied to the skin sample | 1% Fenoldopam mesylate (based on prototype 4B) | 2% Fenoldopam mesylate (based on prototype 4D) | 1% Fenoldopam mesylate (based on prototype 9C) | 2% Fenoldopam mesylate (based on prototype 9F) |
| 24 hrs | 0.000 | 0.000 | 0.007 | 0.027 |
| 48 hrs | 0.000 | 0.002 | 0.007 | 0.029 |

It was concluded that a significant penetration of Fenoldopam to the epidermis was observed in both anhydrous and O/W emulsion formulations. Furthermore, the permeation through the skin to the receptor cell was very low in both formulations, with higher percentage of permeation observed in the O/W formulation.

Example 4: Efficacy of Fenoldopam Mesylate Compositions for the Treatment of Psoriasis The efficacy of the topical stable Fenoldopam compositions developed according to the current disclosure for the treatment of psoriasis is evaluated in a human skin xenotransplant model in mice. Human skin xenotransplant models are optimally suited for performing preclinical assays that explore novel anti-psoriatic agents/treatment strategies before initiating clinical trials. The purpose of this study is to evaluate the effectiveness of Fenoldopam mesylate formulations on the histological parameters of psoriasis in the human T-cell-driven model of psoriasis.

5.1 Study Protocol

The patients included in the study have classic plaque psoriasis, and were not treated for the disease. Normal skin from one healthy volunteer is obtained for grafting.

Healthy human skin pieces with a width of 0.4 mm and surface area of 1.5×1.5 cm are provided from residual skin of routine plastic surgery procedures from the Plastic Surgery Department of the Rambam Health Care Campus, Haifa, Israel. In addition, 20 mL blood samples were taken from the psoriatic patients.

The normal healthy human donor skin is transplanted onto the Beige-severe combined immuno-deficient mice (SCID) (weight ~20 g).

The mice are divided into several treatment groups. Mice of each group receive activated allogeneic T-cells expressing high levels of NK cells receptors from the psoriatic donor.

Peripheral Blood Mononuclear Cells (PBMCs) from the psoriatic patients' blood are isolated and cultured in the presence of a high dose of IL-2 (100 U/mL of media) for 14 days to activate allogeneic T-cells expressing high levels of NK cells receptors.

Four weeks following the engraftment, each mouse is injected with $1 \times 10^7$ activated allogeneic IL2-enriched PBMCS from psoriatic patients ($1 \times 10^7$ cells injected/mouse). Cells from different psoriasis patients are distributed equally between treatment groups. Each patient is represented in each treatment group.

Two weeks following the injections, the mice are divided randomly and treated daily for 14 constitutive days with the different topical formulations.

Fourteen days after starting the treatment (four weeks following the injections), blood samples are taken and the skin is harvested. The grafts are analyzed histologically and immunohistochemically for psoriatic parameters.

Example 5: Efficacy of Fenoldopam Mesylate Compositions for the Treatment of Atopic Dermatitis The efficacy of the topical stable Fenoldopam compositions successfully developed according to the current disclosure is evaluated in an animal model for atopic dermatitis. Repeated 2,4-dinitrochlorobenzene, (DNCB) applications is a common animal model of atopic dermatitis which possesses benefits of reproducibility.

6.1 Study Protocol

Balb/c mice are sensitized on Day 1 by application of 100 μl of 1% DNCB in acetone:olive oil (Figaro) 3:1 on shaved dorsal back skin and 100 μl of 1% DNCB on right ear from day 1 to day 4. On day 6, animals are weighed using digital weighing balance.

After 4 hours of treatment, animals are challenged by application of 1000 of 0.5% DNCB in acetone:olive oil (3:1) on their dorsal back skin and 20 μL of 0.5% DNCB on their right ear on day 8, day 10, day 12, day 14. Normal control animals are sensitized and challenged with acetone and olive oil alone, while the animals in the treatment group are treated with Fenoldopam composition. The composition is applied in around 5-6 cm² area on the back skin of the mice for 9 days from day 6 to day 14. Respective placebo items are topically applied in around 5-6 cm² area on the back skin of the mice for 9 days from day 6 to day 14. Bethamethasone valerate cream is used similarly as a reference.

A clinical scoring is performed to determine the efficacy of tested compositions with appropriate controls. On day 15, back skin severity scores are assessed according to the following criteria 1) Erythema (0-3), 2) Excoriation/Erosion (0-3), 3) Scarring/Dryness, whereas within each criteria the scoring is no lesion, 0; mild, 1; moderate, 2; severe, 3. Total maximum cumulative score is 9 as defined as the sum of these individual scores.

At the end of the study, animals are sacrificed and back skin tissues are harvested for further histological and immunohistochemical analysis for atopic dermatitis parameters.

Example 6: Treatment of Psoriasis with Fenoldopam Mesylate

This study was focused on the effect of Fenoldopam Mesylate (FMT) on experimentally induced psoriasis. In this model, a psoriasis-like phenotype is induced in normal human skin grafted onto beige-severe combined immuno-deficient mice by intradermal injection of natural killer/T-cells derived from psoriatic patients (Gilhar et al., J Invest Dermatol. 2002 August; 119(2):384-91).

The purpose of these further experiments was to verify the therapeutic effect of FMT and compare the therapeutic effects of two doses (1% versus 2%) of two different formulations (cream versus gel).

In order to address the aim of the experiment, the psoriatic humanized mice were established. 10 psoriatic patients were recruited (seven males and three females), mean age 44 years, ranging from 22 to 61 years for testing. All patients had classic plaque psoriasis. None of the patients had been treated. Normal skin from one healthy volunteer was obtained for grafting.

The experiment comprised 72 mice divided into eight groups (Table 10). All of the mice were injected with T-cells expressing NK receptors obtained from psoriatic patients according to the protocol. Thereafter, the mice were separated as follows: Group 1: non-treated control; Group 2: dexamethasone; Group 3: FMT Gel 1%; Group 4: FMT Gel 2%; Group 5: Gel (vehicle); Group 6: FMT Cream 1%; Group 7: FMT Cream 2%; and Group 8: Cream (vehicle). All groups were treated from day 14 until day 28 post T-cells injection.

TABLE 10

Therapeutic effect of FMT-Treatment groups

| Group | Compound | Route | Frequency | Amount of Formulation Applied | Number of Mice |
|---|---|---|---|---|---|
| 1 | Non-treated control | Topical | bid | NA | 6 |
| 2 | Dexamethasone (D2915, Sigma) | Topical | bid | 40 μl | 6 |
| 3 | FMT Gel 1% | Topical | bid | 90 mg | 10 |
| 4 | FMT Gel 2% | Topical | bid | 90 mg | 10 |
| 5 | Gel (vehicle) | Topical | bid | NA | 10 |
| 6 | FMT Cream 1% | Topical | bid | 90 mg | 10 |

TABLE 10-continued

Therapeutic effect of FMT-Treatment groups

| Group | Compound | Route | Frequency | Amount of Formulation Applied | Number of Mice |
|---|---|---|---|---|---|
| 7 | FMT Cream 2% | Topical | bid | 90 mg | 10 |
| 8 | Cream (vehicle) | Topical | bid | NA | 10 |

* From day 14 until day 28 post T-cells injection.

As expected, all of the xenotransplants treated with the various vehicles displayed typical psoriatic features on histology, including epidermal hyperkeratosis and parakeratosis, acanthosis, elongation of rete ridges, and a dense mononuclear infiltrate in the dermis (Tables 11, 12). All of these characteristics were absent in all xenotransplants treated with dexamethasone (Tables 11, 12).

TABLE 11

Histological evaluation of human skin grafts following treatment.

| Group | Compound | Amount of formulation applied | Psoriatic Features | Partial Recovery | Complete Recovery |
|---|---|---|---|---|---|
| 1 | Non treated control | NA | 5/6 | 1/6 | 0/6 |
| 2 | Dexamethasone | 40 µl | 0/6 | 1/6 | 5/6 |
| 3 | FMT Gel 1% | 90 mg | 5/10 | 1/10 | 4/10 |
| 4 | FMT Gel 2% | 90 mg | 4/10 | 1/10 | 5/10 |
| 5 | Gel (vehicle) | NA | 9/10 | 0/10 | 1/10 |
| 6 | FMT Cream 1% | 90 mg | 5/10 | 1/10 | 4/10 |
| 7 | FMT Cream 2% | 90 mg | 5/10 | 0/10 | 5/10 |
| 8 | Cream (vehicle) | NA | 9/10 | 0/10 | 1/10 |

TABLE 12

Epidermal thickness measurements (um) from normal skin xenografted and psoriatic patient T-cell injected beige-SCID mice.

| Donor | Non-treated control | Dexa (2 mg) | FMT Gel 1% | FMT Gel 2% | Gel (vehicle) | FMT Cream 1% | FMT Cream 2% | Cream (vehicle) |
|---|---|---|---|---|---|---|---|---|
| 1 | 848 | 338 | 446 | 298 | 628 | 350 | 722 | 240 |
| 2 | 602 | 280 | 220 | 338 | 1250 | 258 | 259 | 643 |
| 3 | 540 | 290 | 762 | 212 | 657 | 550 | 643 | 880 |
| 4 | 620 | 300 | 765 | 760 | 756 | 709 | 218 | 513 |
| 5 | 850 | 305 | 720 | 787 | 682 | 134 | 459 | 532 |
| 6 | 780 | 260 | 322 | 206 | 405 | 536 | 134 | 694 |
| 7 | | | 642 | 554 | 721 | 279 | 536 | 640 |
| 8 | | | 594 | 438 | 471 | 536 | 640 | 624 |
| 9 | | | 376 | 699 | 768 | 280 | 714 | 712 |
| 10 | | | 250 | 220 | 460 | 594 | 280 | 707 |
| Mean | 706 | 295* | 509 | 451** | 680 | 422*** | 460 | 618 |
| STDEV | 135 | 26 | 212 | 232 | 238 | 188 | 221 | 167 |

Comparison test - Kruskal-Wallis test, followed by a Mann-Whitney U test.
*Dexamethasone versus non-treated and all treated groups - $P<0.002$ and $p<0.03$, respectively.
**FMT(Gel) 2%, Group 4 versus non-treated control and vehicle (Gel) - $p<0.02$.
***FMT(cream) 1%, Group 6 versus non-treated control and vehicle (Vream) - $p<0.04$.

Xenotransplants treated with FMT Gel 2% displayed recovery from the psoriasiform features in 6/10 mice with mean epidermal thickness of 451±232 µm (Tables 11, 12). Similarly, xenotransplants treated with FMT Gel 1% displayed recovery in 5/10 mice with mean epidermal thickness of 509±212 µm. Xenotransplants treated with vehicle (Gel) demonstrated psoriasiform features in 9 grafts (9/10) with increased mean epidermal thickness=680±238 µm (Tables 11, 12). Therapeutic effects were also observed by using cream instead of gel. Xenotransplants treated with FMT Cream 1% demonstrated cleaning of psoriatic features in 5/10 xenotransplants and 422±188 µm epidermal thickness. Treatment with Cream 2% demonstrated complete recovery in five xenotransplants (5/10) mean epidermal thickness of 460±221. However, xenotransplants treated with vehicle (Cream) demonstrated complete recovery in only one xenotransplant versus 9/10 with psoriatic features and a high level of mean epidermal thickness, 618±167 µm, Tables 11, 12). Conversely, xenotransplants treated with dexamethasone showed complete (5/6) or partial (1/6) recovery from the psoriatic features with 295±26 μm mean epidermal thickness.

We then stained skin sections derived from the various human xenotransplants for Ki-67 and HLA-DR: the first, a marker of cellular hyperproliferation and the second, for immune stimulation. Strong expression of Ki-67 was observed along the lower part of the epidermis in all control and vehicle groups and in the non-responders FMT xenotransplants. Weaker expression was observed in the dexamethasone group and in the FMT responders xenotransplants (FIG. 1). As shown in FIG. 1 and Tables 13 and 14, HLA-DR was found to be expressed strongly throughout the epidermis of xenotransplants treated with various control and vehicle and in most of the non-responders xenotransplants. However, weak or absent HLA-DR expression was observed along the epidermis in the responders transplants treated with FMT. More specifically, 6/10 FMT Gel 2%-treated xenotransplants demonstrated mild or complete negative HLA-DR expression along the epidermis. Cream 2% down-regulated epidermal HLA-DR expression in 5/10 xenotransplants (FIG. 1 and Tables 13, 14).

TABLE 13

HLA-DR induction by the epidermis.

| | Epidermal HLA-DR Expression | | | |
|---|---|---|---|---|
| Compound | Negative | Focal[1] | Diffuse[2] | Total Number of Grafts |
| Control (non-treated) | 0/6 | 1/6 | 5/6 | 6 |
| Dexamethasone | 5/6 | 1/6 | 0/6 | 6 |
| Group 4, FMT Gel 2% | 4/10 | 2/10 | 4/10 | 10 |
| Group 5, Vehicle (Gel) | 1/10 | 1/10 | 8/10 | 10 |
| Group 7, FMT Cream 2% | 4/10 | 1/10 | 5/10 | 10 |
| Group 8, Vehicle (Cream) | 1/10 | 0/10 | 9/10 | 10 |

[1]Focal—less than 50% of the epidermal area
[2]Diffuse—more than 50% of the epidermal area

TABLE 14

HLA-DR positive cells along the dermis.

| | Dermal HLA-DR Expression | | | |
|---|---|---|---|---|
| Compound | Negative | Mild | Dense | Total Number of Grafts |
| Control (non-treated) | 0/10 | 2/6 | 4/6 | 6 |
| Dexamethasone | 4/6 | 2/6 | 0/6 | 6 |
| Group 4, FMT Gel 2% | 4/10 | 3/10 | 3/10 | 10 |
| Group 5, Vehicle (Gel) | 1/10 | 0/10 | 9/10 | 10 |
| Group 7, FMT Cream 2% | 4/10 | 1/10 | 5/10 | 10 |
| Group 8, Vehicle (Cream) | 1/10 | 1/10 | 8/10 | 10 |

Negative expression—no staining
Mild—minor level of cell infiltrates of positive cells along the dermis
Dense—intense level of cell infiltrates of positive cells along the dermis To characterize the inflammatory infiltrate in the skin, we examined the expression of CD8, CD4 and IL-17+ cells, which mark T lymphocytes (FIG. 1 and Tables 15, 16). These markers were found to be expressed strongly in the upper part of the dermis of the various control and vehicle groups, as well as in the non-responders xenotransplants treated with FMT, but weakly, if at all, in xenotransplants treated either with dexamethasone or in the FMT responders' grafts. More precisely, weak or absent expression of HLA-DR and CD4+ cells was observed in 6/10 and 7/10 responders xenotransplants treated with FMT Gel 2% (FIG. 1 and Tables 15, 16).

TABLE 15

CD8, CD4 and IL-17 positive cells along the dermis.

| | CD8 | | | CD4 | | | IL-17 | | |
|---|---|---|---|---|---|---|---|---|---|
| Compound | Negative | Mild | Dense | Negative | Mild | Dense | Negative | Mild | Dense |
| Control (Non treated) | 0/10 | 1/6 | 5/6 | 0/10 | 1/6 | 5/6 | 0/10 | 1/6 | 5/6 |
| Dexamethasone | 5/6 | 1/6 | 0/10 | 4/6 | 2/6 | 0/10 | 5/6 | 1/6 | 0/10 |
| Group 4, FMT Gel 2% | 5/10 | 2/10 | 3/10 | 5/10 | 1/10 | 4/10 | 5/10 | 1/10 | 4/10 |
| Group 5, Vehicle (Gel) | 1/10 | 0/10 | 9/10 | 1/10 | 1/10 | 8/10 | 1/10 | 1/10 | 8/10 |
| Group 7, FMT Cream 2% | 4/10 | 1/10 | 5/10 | 4/10 | 1/10 | 5/10 | 4/10 | 2/10 | 4/10 |
| Group 8, Vehicle (Cream) | 1/10 | 1/10 | 8/10 | 1/10 | 0/10 | 9/10 | 1/10 | 0/10 | 9/10 |

Negative expression - no staining
Mild - minor level of cell infiltrates of positive cells along the dermis
Dense - intense level of cell infiltrates of CD8+, CD4+ IL17+ positive cells along the dermis

TABLE 16

HLA-DR CD8, CD4 and IL-17 positive cells in the responders and non-responders grafts.

|  |  | Dermal HLA-DR Expression | | CD8 Expression | | CD4 Expression | | IL-17 Expression | |
|---|---|---|---|---|---|---|---|---|---|
|  |  | Negative/Mild | Dense | Negative/Mild | Dense | Negative/Mild | Dense | Negative/Mild | Dense |
| Compound Control (non-treated) | Responders (0/6) | 0/6 | 0/6 | 0/6 | 0/6 | 0/6 | 0/6 | 0/6 | 0/6 |
|  | Non responders (6/6) | 1/6 | 5/6 | 1/6 | 5/6 | 1/6 | 5/6 | 1/6 | 5/6 |
| Dexamethasone | Responders (6/6) | 6/6 | 0/6 | 6/6 | 0/6 | 6/6 | 0/6 | 6/6 | 0/6 |
|  | Non responders (0/6) | 0/6 | 0/6 | 0/6 | 0/6 | 0/6 | 0/6 | 0/6 | 0/6 |
| Group 4, FMT Gel 2% | Responders (5/10) | 5/5 | 0/5 | 5/5 | 0/5 | 5/5 | 0/5 | 5/5 | 0/5 |
|  | Non responders (5/10) | 1/5 | 4/5 | 2/5 | 3/5 | 1/5 | 4/5 | 1/5 | 4/5 |
| Group 5, Vehicle (Gel) | (1/10) | 1/1 | 0/1 | 1/1 | 0/1 | 1/1 | 0/1 | 1/1 | 0/1 |
|  | Non responders (9/10) | 1/9 | 8/9 | 0/9 | 9/9 | 1/9 | 8/9 | 1/9 | 8/9 |
| Group 7, FMT Cream 2% | Responders (5/10) | 5/5 | 0/5 | 5/5 | 0/5 | 5/5 | 0/5 | 5/5 | 0/5 |
|  | Non responders (5/10) | 0/5 | 5/5 | 0/5 | 5/5 | 0/5 | 5/5 | 1/5 | 4/5 |
| Group 8, Vehicle (Cream) | Responders (1/10) | 1/1 | 0/1 | 1/1 | 0/1 | 1/1 | 0/1 | 1/1 | 0/1 |
|  | Non responders (9/10) | 0/9 | 9/9 | 1/9 | 8/9 | 0/9 | 9/9 | 0/9 | 9/9 |

Xenotransplants treated with Cream 2% demonstrated weak or absent CD8+ and CD4+ cells along the upper dermis in 5/10 and IL-17+ cells in 6/10 transplants (FIG. 1 and Tables 15, 16). As mentioned above, expressions of the inflammatory markers were observed in all the control and vehicle groups (Control non-treated, vehicle gel and vehicle cream), further supporting the therapeutic intervention of FMT. These findings suggest a possible effect of FMT on the immune elements of psoriasis.

In conclusion, the study confirmed a possible therapeutic effect of FMT in the humanized mouse model for psoriasis for both gel and cream formulations.

Example 7: Long-Term Stability of Fenoldopam Topical Compositions

To evaluate the long term stability of the composition, composition samples are kept at RT conditions. INT conditions, or ACC conditions for an extended period of time. The physical stability was evaluated by maintaining the consistency in the macroscopic and microscopic appearance of the compositions (including parameters such as color, homogeneity, lack of phase separation, absence of crystals, droplet size for emulsions) and in characteristics such as pH (in aqueous compositions) and thixotropic properties (including for example spreadability). The chemical stability is evaluated by consistency in the levels of Fenoldopam (the Assay results) and in the levels of known and unknown impurities, as well as preservative levels, measured during these storage periods using HPLC technique.

The disclosure is exemplified by anhydrous formulations (gels) as outlined in Table 17.

TABLE 17

Anhydrous Formulations

| | Formulation | | | | | |
|---|---|---|---|---|---|---|
| | 1 | 2 | 3 | 4 | 5 | 6 |
| Fenoldopam Mesylate | 1% | 1% | 1% | 1% | 2% | 2% |
| Propylene glycol | 40.00 | 40.00 | 20.00 | 0 | 40.00 | 40.00 |
| Hexylene glycol | 0 | 0 | 20.00 | 40.00 | 0 | 0 |
| HydroxyPropyl Cellulose (Klucel LF) | 2.50 | 0 | 2.50 | 2.50 | 2.50 | 0 |
| Hydroxypropyl methyl cellulose | 0 | 2.50 | 0 | 0 | 0 | 2.50 |
| Sorbic Acid | 0.05 | 0.05 | 0.05 | 0.05 | 0.05 | 0.05 |
| Sepineo P600 | 2.50 | 2.50 | 2.50 | 0 | 2.50 | 2.50 |
| Sepigel 305 | 0 | 0 | 0 | 2.50 | 0 | 0 |

TABLE 17-continued

| Anhydrous Formulations | | | | | | |
|---|---|---|---|---|---|---|
| Glycerin USP | 15.00 | 15.00 | 15.00 | 15.00 | 20.00 | 20.00 |
| PPG-15 Stearyl ether | 8.00 | 8.00 | 0 | 8.00 | 3.00 | 3.00 |
| PPG-12/SDMI copolymer | 0 | 0 | 8.00 | 0 | 0 | 0 |
| PEG 400 NF | 30.95 | 30.95 | 30.95 | 30.95 | 29.95 | 29.95 |

| | Formulation | | | | | | | |
|---|---|---|---|---|---|---|---|---|
| | 7 | 8 | 9 | 10 | 11 | 12 | 13 | 14 |
| Fenoldopam Mesylate | 2% | 2% | 2% | 2% | 2% | 2% | 2% | 2% |
| Propylene glycol | 0 | 40.00 | 0 | 20.00 | 40.00 | 20.00 | 40.00 | 40.00 |
| Hexylene glycol | 40.00 | | 40.00 | 20.00 | | 20.00 | | |
| HydroxyPropyl Cellulose (Klucel LF) | 2.50 | 2.50 | 2.50 | 0 | 2.50 | 0 | 2.50 | 2.50 |
| Hydroxypropyl methyl cellulose | 0 | 0 | 0 | 2.50 | 0 | 2.50 | | |
| Sorbic Acid | 0.05 | 0.05 | 0.05 | 0.05 | 0.05 | 0.05 | 0.05 | 0.05 |
| Sepineo P600 | 2.50 | 2.50 | 0 | 2.50 | 2.50 | 0 | 2.50 | 2.50 |
| Sepigel 305 | 0 | 0 | 2.50 | 0 | 0 | 4.50 | | |
| Glycerin USP | 15.00 | 15.00 | 15.00 | 20.00 | 20.00 | 10.00 | 15.00 | 23.00 |
| PPG-15 Stearyl ether | 0 | 8.00 | 0 | 3.00 | 0 | 8.00 | | |
| PPG-12/SDMI copolymer | 8.00 | 0 | 8.00 | 0 | 3.00 | 3.00 | | |
| Octyldodecanol NF | | | | | | | 8.00 | |
| PEG 400 NF | 29.95 | 29.95 | 29.95 | 29.95 | 29.95 | 29.95 | 29.95 | 29.95 |

The disclosure is also exemplified by oil-in-water emulsion formulations (creams) as outlined in Table 18.

TABLE 18

| Oil-in-water emulsions | | | | | | | |
|---|---|---|---|---|---|---|---|
| | Formulation | | | | | | |
| | 15 | 16 | 17 | 18 | 19 | 20 | 21 |
| Fenoldopam Mesylate | 1% | 1% | 1% | 1% | 1% | 1% | 1% |
| Isostearic Acid | 10.00 | 15.00 | 15.00 | 17.00 | 15.00 | 12.50 | 12.50 |
| Sepineo P600 | 4.00 | 4.00 | 4.00 | 3.00 | 0 | 0 | 0 |
| Sepigel 305 | 0 | 0 | 0 | 0 | 5.00 | 4.00 | 4.00 |
| Sorbic Acid | 0.10 | 0.10 | 0.10 | 0.10 | 0.10 | 0.10 | 0.10 |
| Propylene glycol | 14.00 | 0 | 10.00 | 10.00 | 0 | 0 | 3.50 |
| Heylene glycol | 0 | 10.00 | 0 | 0 | 0 | 12.50 | 10.00 |
| Dimethyl Isosorbide | 10.00 | 10.00 | 10.00 | 0 | 0 | 0 | 0 |
| Purified water | 58.90 | 58.90 | 58.90 | 58.90 | 58.90 | 58.90 | 58.90 |
| Hydroxypropyl Cellulose (Klucel LF) | 0 | 1.00 | 1.00 | 0 | 0 | 0 | 1.0 |
| Hydroxypropyl methyl cellulose | 2.00 | 0 | 0 | 0 | 0 | 0 | 1.0 |
| Ethyl cellulose | 0 | 0 | 0 | 1.0 | 1.0 | 2.0 | 0 |
| NaOH 1N | q.s | q.s | q.s | q.s | q.s | q.s | q.s |
| | 22 | 23 | 24 | 25 | 26 | 27 | 28 |
| Fenoldopam Mesylate | 2% | 2% | 2% | 2% | 2% | 2% | 2% |
| Isostearic Acid | 10.00 | 15.00 | 15.00 | 17.00 | 15.00 | 12.50 | 12.50 |
| Sepineo P600 | 4.00 | 0 | 4.00 | 3.00 | 4.00 | 0 | 0 |
| Sepigel 305 | 0 | 4.00 | 0 | 0 | 0 | 3.00 | 4.00 |
| Fenoldopam Mesylate | 2.00 | 2.00 | 2.00 | 2.00 | 2.00 | 2.00 | 2.00 |
| Sorbic Acid | 0.10 | 0.10 | 0.10 | 0.10 | 0.10 | 0.10 | 0.10 |
| Propylene glycol | 10.00 | 10.00 | 0 | 0 | 10.00 | 0 | 10.00 |
| Heylene glycol | 0 | 0 | 10.00 | 10.00 | 0 | 10.00 | 0 |
| Dimethyl Isosorbide | 10.00 | 10.00 | 10.00 | 10.00 | 10.00 | 10.00 | 10.00 |
| Purified water | 57.90 | 56.90 | 57.90 | 57.90 | 57.90 | 59.90 | 59.90 |
| Hydroxypropyl Cellulose (Klucel LF) | 1.00 | 0 | 0 | 0 | 1.00 | 0 | 0 |
| Hydroxypropyl methyl cellulose | 0 | 2.00 | 1.00 | 0 | 0 | 0 | 1.50 |
| Ethyl cellulose | 0 | 0 | 0 | 2.00 | 0 | 2.50 | 0 |
| NaOH 1N | q.s | q.s | q.s | q.s | q.s | q.s | q.s |

Analysis at T=0, 2 weeks for anhydrous Formulation 1 is presented in Table 19A, and T=0, 2 weeks, 1 month, 2 months, 3 months and 9 months for anhydrous Formulation 8 is presented in Table 19B:

TABLE 19A

Formulations 1-Anhydrous gel

| | Formulation 1 | |
|---|---|---|
| | T = 0 | 2 W 50 C |
| % Fenoldopam Assay | 96 | 95.3 |
| % Impurity B | 0.10 | 0.11 |
| % Total Impurities | 0.9 | 0.98 |
| viscosity (cP) | 18788 | 16882 |

TABLE 19B

Formulation 8 Anhydrous gel

| | T = 0 | 2W 50° C. | T = 1m RT | T = 2 m Acc | T = 3 m RT | T = 3 m Acc | T = 9 m RT |
|---|---|---|---|---|---|---|---|
| % Fenoldopam Assay | 97.1 | 97.1 | 95.2 | 95.2 | 93.9 | 94.6 | 89.1 | 96.2 |
| % Impurity B | 0.09 | 0.12 | 0.09 | 0.09 | 0.09 | 0.09 | 0.09 | 0.09 |
| % Total Impurities | 0.93 | 0.83 | 0.81 | 0.81 | 0.76 | 0.90 | 0.91 | 0.79 |
| viscosity (cP) | 17170 | 15216 | 14228 | 15748 | 19,604 | not tested | not tested | 16310 cP |

Analysis at T=0, 2 weeks, 1 month and 3 months for Formulations 11, 13 and 14 is presented in Table 20, Table 20A and Table 20B.

Table 20

Formulation 11 Anhydrous gel

| | T = 0 | 2 W 50 C | T = 1 m Acc | T = 3 m Int | T = 3 m Acc |
|---|---|---|---|---|---|
| % Fenoldopam Assay | 103.4 | 105.5 | 99.8 | 102 | 102.2 |
| % Impurity B | 0.1 | 0.11 | 0.11 | 0.1 | 0.12 |
| % Total Impurities | 0.19 | 0.24 | 0.35 | 0.18 | 0.48 |
| Viscosity | 14560 cP | 14274 cP | 14680 cP | 14444 cP | 15806 cP |

TABLE 20A

Formulation 13 Anhydrous gel

| | T = 0 | T = 1 m Acc | T = 3 m Int | T = 3 m Acc |
|---|---|---|---|---|
| % Fenoldopam Assay | 102.2 | 107.6 | 104.9 | 109.5 |
| % Impurity B | 0.09 | 0.11 | 0.1 | 0.12 |
| % Total Impurities | 0.16 | 0.20 | 0.18 | 0.55 |
| Viscosity | 16150 cP | 16648 cP | 13474 cP | 14660 cP |

TABLE 20B

Formulation 14 Anhydrous gel

| | T = 0 | T = 1 m Acc | T = 3 m Int | T = 3 m Acc |
|---|---|---|---|---|
| % Fenoldopam Assay | 101.7 | 101.6 | 99 | 100 |
| % Impurity B | 0.10 | 0.11 | 0.1 | 0.12 |
| % Total Impurities | 0.15 | 0.18 | 0.16 | 0.43 |
| Viscosity | 12544 cP | 12338 cP | 14424 cP | 12182 cP |

Analysis at T=0, 2 weeks, 1 month, 2 months, 3 months, 6 months and 9 months for representative oil-in-water formulation from Table 18 is presented in Table 21 and Table 22:

TABLE 21

Stability of representative oil-in-water formulation from Table 18

| | | | T = 1m | | | T = 2 m | |
|---|---|---|---|---|---|---|---|
| | T = 0 | 2W 50C | RT | INT | ACC | INT | ACC |
| % Fenoldopam Assay | 97.8 | 96.4 | 96.9 | 96.8 | 96.4 | 97.4 | 96.9 |
| % Impurity B | 0.11 | 0.15 | 0.10 | 0.10 | 0.12 | 0.11 | 0.15 |
| % Total Impurities | 0.11 | 0.28 | 0.10 | 0.10 | 0.16 | 0.11 | 0.27 |
| pH | 4.18 | 4.11 | 4.2 | 4.2 | 4.1 | 4.1 | 4.1 |
| viscosity (cP) | 99064 | 86102 | not tested | not tested | 88,726 | not tested | 86,664 |

| | T = 3 m | | | T = 6 m | | | T = 9 m | | T = 12 m | |
|---|---|---|---|---|---|---|---|---|---|---|
| | RT | INT | ACC | RT | INT | ACC | RT | INT | RT | INT |
| % Fenoldopam Assay | 98.6 | 98.6 | 98.2 | 97.9 | 97.5 | 96.1 | 98.2 | 97.7 | 101.9 | 100.9 |
| % Impurity B | 0.11 | 0.12 | 0.17 | 0.12 | 0.13 | 0.25 | 0.11 | 0.13 | 0.12 | 0.14 |
| % Total Impurities | 0.11 | 0.12 | 0.35 | 0.16 | 0.24 | 0.86 | 0.19 | 0.25 | 0.17 | 0.28 |
| pH | 4.1 | 4.1 | 4.2 | 4.1 | 4.07 | 4.1 | 4.16 | 4.13 | 4.13 | 4.12 |
| viscosity (cP) | 96,860 | not tested | 81,767 | not tested | not tested | not tested | not tested | not tested | not tested | not tested |

TABEL 22

Representative oil-in-water formulation from Table 18

| | | | T = 1m | | | T = 2 m | |
|---|---|---|---|---|---|---|---|
| | T = 0 | 2W 50C | RT | INT | ACC | RT | INT |
| % Fenoldopam Assay | 98.8 | 96.5 | 96.5 | 96.3 | 96.2 | 97.4 | 96.8 |
| % Impurity B | 0.13 | 0.18 | 0.13 | 0.13 | 0.16 | 0.13 | 0.18 |
| % Total Impurities | 0.18 | 0.47 | 0.31 | 0.35 | 0.37 | 0.28 | 0.42 |
| pH | 4.18 | 4.1 | 4.2 | 4.2 | 4.1 | 4.1 | 4 |
| viscosity (cP) | 5483 | 3308 | 4690 | 4709 | 3426 | 4682 | 3273 |

| | T = 3 m | | | T = 6 m | | | T = 9 m | | T = 12 m | |
|---|---|---|---|---|---|---|---|---|---|---|
| | RT | INT | ACC | RT | INT | ACC | RT | INT | RT | INT |
| % Fenoldopam Assay | 98.8 | 98.5 | 97.9 | 97.9 | 97.3 | 95.8 | 97.8 | 97.1 | 101.8 | 101 |
| % Impurity B | 0.13 | 0.13 | 0.13 | 0.14 | 0.14 | 0.14 | 0.15 | 0.18 | 0.15 | 0.2 |
| % Total Impurities | 0.33 | 0.38 | 0.60 | 0.34 | 0.67 | 1.24 | 0.42 | 0.53 | 0.40 | 0.61 |
| pH | 4.1 | 4.1 | 4.05 | 4.12 | 4.05 | 4 | 4.16 | 4.06 | 4.08 | 4.13 |
| viscosity (cP) | 4816 | 4709 | 3469 | 4980 | 4165 | 3367 | 4869 | 4342 | 4278 | 5038 |

The stability studies suggest the tested anhydrous gels as well as oil-in-water emulsions tested comprising at least one polyacrylamide-type gelling agent, at least one cellulose-type gelling agent, and at least one solvent are stable for up to 12 months.

What is claimed is:

1. A topical composition of Fenoldopam comprising about 0.1% to about 5% by weight of Fenoldopam or a pharmaceutically acceptable salt thereof, at least one polyacrylamide-type gelling agent, at least one cellulose-type gelling agent, and at least one solvent, wherein the Fenoldopam is substantially solubilized in the composition, and wherein the composition is physically and chemically stable for at least one month at 25° C. and 60% relative humidity.

2. The topical composition of claim 1, wherein the Fenoldopam pharmaceutically acceptable salt is Fenoldopam mesylate.

3. The topical composition according to claim 1, comprising about 1% to about 3% by weight of Fenoldopam or a pharmaceutically acceptable salt thereof.

4. The topical composition according to claim 1, wherein the amount of the at least one polyacrylamide-type gelling agent in the composition is about 1% to about 5% by weight of the composition.

5. The topical composition according to claim 1, wherein the amount of the at least one cellulose-type gelling agent in the composition is about 1% to about 5% by weight of the composition.

6. The topical composition according to claim 1, wherein the polyacrylamide-type gelling agent is selected from acrylamide/sodium acryloyldimethyl taurate copolymer/isohexadecane/polysorbate 80 mixture (Sepineo™ P600), polyacrylamide/C13-14 isoparaffin/laureth-7 mixture (Sepigel™ 305), hydroxyethyl acrylate/sodium acryloyldimethyl taurate copolymer mixture (Sepinov™ EMT 10) and hydroxyethyl acrylate/sodium acryloyldimethyl taurate copolymer (Sepineo™ DERM).

7. The topical composition according to claim 6, wherein the polyacrylamide-type gelling agent is acrylamide/sodium acryloyldimethyl taurate copolymer/isohexadecane/polysorbate 80 mixture (Sepineo™ P600).

8. The topical composition according to claim 1, wherein the cellulose-type gelling agent is selected from ethyl cellulose, methyl cellulose, hydroxyethyl cellulose, hydroxypropyl cellulose (Klucel™), hydroxypropyl methylcelluloses, hydroxybutyl methylcellulose, carboxymethylcellulose, and combinations thereof.

9. The topical composition according to claim 1, wherein the composition further comprises at least one co-solvent.

10. The topical composition according to claim 1, wherein the solvent is selected from propylene glycol, dimethyl isosorbide, glycerin, ethanol, polyethylene glycol, hexylene glycol, diethylene glycol monoethyl ether and combinations thereof.

11. The topical composition according to claim 1, wherein the composition further comprises at least one emollient.

12. The topical composition according to claim 1, wherein at least 80% by weight of the Fenoldopam or a pharmaceutically acceptable salt thereof is solubilized.

13. The topical composition according to claim 1, wherein the weight % of Fenoldopam in the composition is reduced by less than about 10% after one month at 25° C. and 60% relative humidity.

14. The topical composition according to claim 1, wherein the weight percentage of Fenoldopam in the composition is between 90%-110% of a label claim of Fenoldopam for at least one month.

15. The topical composition according to claim 1, wherein the composition comprises less than about 1% by weight impurity B after at least one month at 25° C. and 60% relative humidity.

16. The topical composition according to claim 1, wherein the composition is homogenous for at least one month at 25° C. and 60% relative humidity.

17. The topical composition according to claim 1, wherein the dosage form is an ointment, cream, lotion, gel, spray, foam, cloth, patch, wipe or pad.

18. The topical composition according to claim 1, wherein the pH of the composition is from about 4 to about 5 after at least one month at 25° C. and 60% relative humidity.

19. The topical composition according to claim 1, wherein the composition further comprises at least one preservative, at least one penetration enhancer, at least one stabilizer, at least one viscosity-increasing agent, at least one thickener, at least one foaming agent, at least one chelating agent or at least one antioxidant.

20. A method of treating a D1 receptor- mediated skin disorder in a subject in need thereof, the method comprising topically administering the composition of claim 1 to an affected skin area of the subject, wherein the D1 receptor-mediated skin disorder is selected from psoriasis, atopic dermatitis, alopecia, acne, rosacea and vitiligo.

* * * * *